(12) United States Patent
Agou et al.

(10) Patent No.: US 7,700,553 B2
(45) Date of Patent: *Apr. 20, 2010

(54) SELECTIVE INHIBITION OF NF-κB ACTIVATION BY PEPTIDES DESIGNED TO DISRUPT NEMO OLIGOMERIZATION

(75) Inventors: Fabrice Agou, Paris (FR); Gilles Courtois, Paris (FR); Alain Israel, Paris (FR); Michel Veron, Paris (FR); Francois Traincard, Issy-les-Moulineaux (FR); Shoji Yamaoka, Fuchu (JP); Yves-Marie Coic, Meudon (FR); Francoise Baleux, Paris (FR)

(73) Assignees: Institut Pasteur, Paris (FR); INSERM (Institut National de la Sante et de la Recherche Medicale), Paris (FR); Centre National De La Recherche Scientifique, Paris (FR)

( * ) Notice: Subject to any disclaimer, the term of this patent is extended or adjusted under 35 U.S.C. 154(b) by 563 days.

This patent is subject to a terminal disclaimer.

(21) Appl. No.: 10/573,161

(22) PCT Filed: Sep. 24, 2004

(86) PCT No.: PCT/IB2004/003352

§ 371 (c)(1),
(2), (4) Date: Mar. 1, 2007

(87) PCT Pub. No.: WO2005/027959

PCT Pub. Date: Mar. 31, 2005

(65) Prior Publication Data

US 2008/0242601 A1    Oct. 2, 2008

Related U.S. Application Data

(60) Provisional application No. 60/505,161, filed on Sep. 24, 2003, provisional application No. 60/530,418, filed on Dec. 18, 2003.

(51) Int. Cl.
*C07K 1/00* (2006.01)
*A61K 38/00* (2006.01)

(52) U.S. Cl. .................................. 514/12; 530/350
(58) Field of Classification Search .................. 530/350; 514/12

See application file for complete search history.

(56) References Cited

U.S. PATENT DOCUMENTS

2005/0220792 A1   10/2005   Agou et al.

FOREIGN PATENT DOCUMENTS

| WO | 99/47672 | 9/1999 |
| WO | 01/83554 | 11/2001 |
| WO | 02/092761 | 11/2002 |

OTHER PUBLICATIONS

Tegethoff, Sebastian et al., "Tetrameric Oligomerization of IkB Kinase gamma (IKKgamma)is obligatory for IKK complex Activity and NF-κB activation", Molecular and Cellular Biology, vol. 23, No. 6, pp. 2029-2041, 2003.

Le Page, Cecile et al., "Disruption of NF-κB Signaling and Chemokine Gene Activation by Retroviral Mediated Expression of IKKgamma/NEMO Mutants", Virology, vol. 286, No. 2, pp. 422-433, 2001.

May, Michael J. et al., "Selective Inhibition of NF-κB Activation by a Peptide That Blocks the Interaction of NEMO with the IkB Kinase Complex", Science, vol. 289, pp. 1550-1554, 2000.

Agou, Fabrice et al., "The Trimerization Domain of Nemo Is Composed of the Interacting C-termianl CC2 and LZ Coiled-coil Subdomains", The Journal of Bilogical Chemistry, vol. 279, No. 27, pp. 27861-27869, 2004.

Iha, Hidekatsu et al., "Segregation of NF-κB activation through NEMO/IKKgamma by Tax TNFalpha: implications for stimulus-specific interruption of oncogenic signaling", Oncogene, vol. 22, No. 55, pp. 8912-8923, 2003.

Agou, Fabrice et al., "Inhibition of NF-κB Activation by Peptides Targeting NF-κB Essential Modulator (NEMO) Oligomerization", The Journal of Biological Chemistry, vol. 279, No. 52, pp. 54248-54257, 2004.

*Primary Examiner*—Maryam Monshipouri
(74) *Attorney, Agent, or Firm*—Oblon, Spivak, McClelland, Maier & Neustadt, L.L.P.

(57) ABSTRACT

The present invention relates to polypeptides that inhibit the NF-&kgr;B signaling pathway and polynucleotides encoding the same. The present invention further provides methods for the modulation of and/or treatment of inflammatory responses, oncogenesis, viral infection; the regulation of cell proliferation and apoptosis; and regulation of B or T lymphocytes in antigenic stimulation, by administering the polypeptides of the present invention to a subject in need thereof. Finally, the present invention provides a method of identifying polypeptides that modulate oligomerization of NEMO.

28 Claims, 8 Drawing Sheets

(A)

(B)

(C)

(D)

(A)

(B)

(A)

(B)

Figure 1:
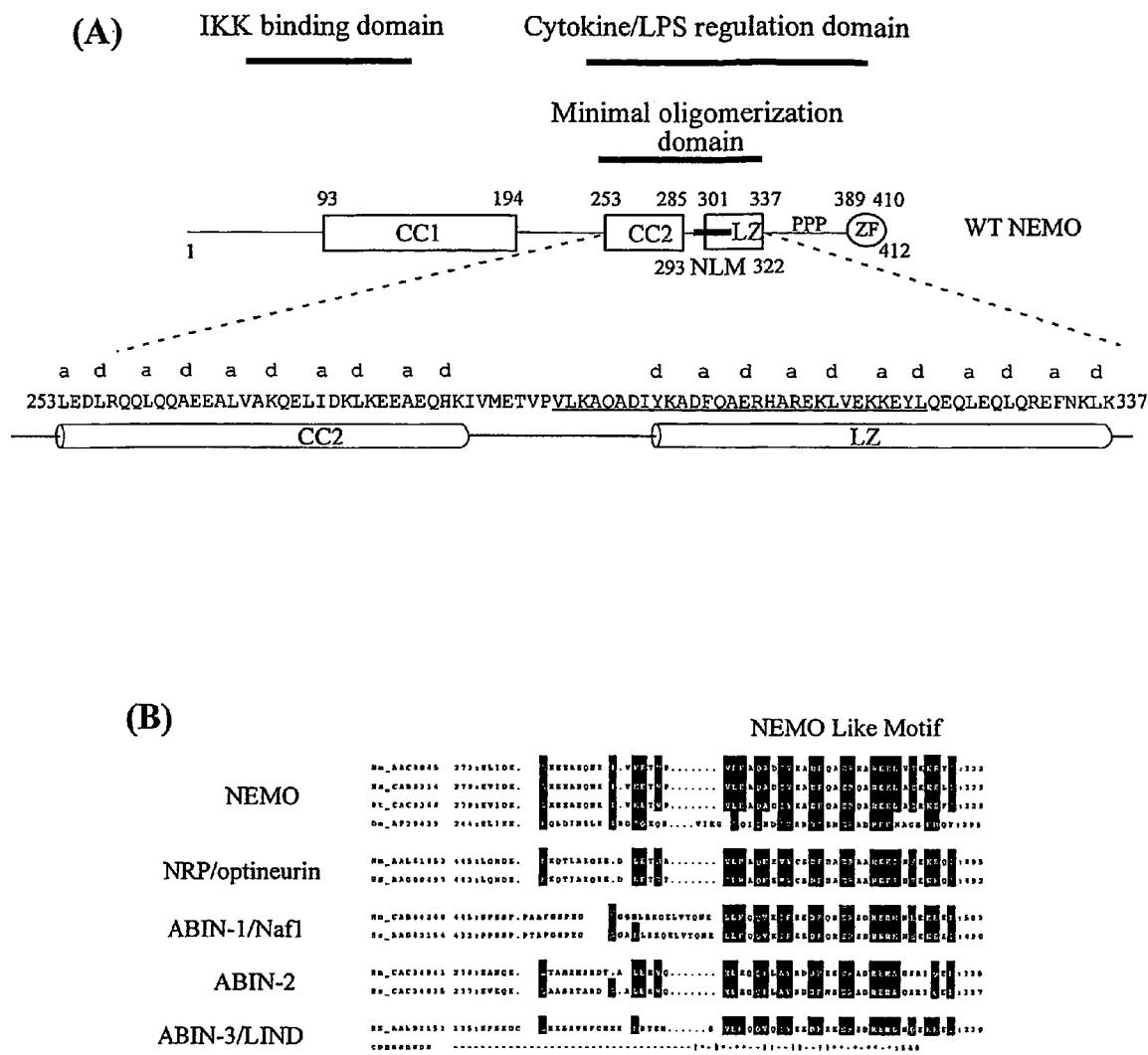

...

SELECTIVE INHIBITION OF NF-κB ACTIVATION BY PEPTIDES DESIGNED TO DISRUPT NEMO OLIGOMERIZATION

This application is a 371 of PCT/IB04/03352 filed Sep. 24, 2004, which claims priority to U.S. Provisional applications 60/505,161 and 60/530,418, filed Sep. 24, 2003 and Dec. 18, 2003 respectively.

The present invention relates to polypeptides that inhibit the NF-κB signaling pathway and polynucleotides encoding the same. The present invention further provides methods for the modulation of and/or treatment of inflammatory responses, oncogenesis, viral infection; the regulation of cell proliferation and apoptosis; and regulation of B or T lymphocytes in antigenic stimulation, by administering the polypeptides of the present invention to a subject in need thereof. Finally, the present invention provides a method of identifying polypeptides that modulate oligomerization of NEMO.

Nuclear factor-κB (NF-κB) signaling is an essential signal transduction pathway involved in inflammatory responses, oncogenesis, viral infection, the regulation of cell proliferation and apoptosis and in the case of B and T lymphocytes in antigenic stimulation (Ghosh, 1998, Annu. Rev. Immunol.; Karin, 1999, J. Biol. Chem.; Israel, 2000, Trends Cell Biol.; Santoro, 2003, EMBO J.). In mammalian cells, there are five NF-κB family members that dimerize: RelA, RelB, c-Rel, NF-κB2/p100/p52 and NF-κB1/p105/p50. NF-κB whose predominant form is a heterodimeric transcription factor composed of p50 and RelA subunits, remains sequestered in the cytoplasm through association with members of an inhibitory family of proteins known as IκB. Upon stimulation by the cytokines TNF-α and interleukin-1, endotoxin (LPS), microbial and viral infections, pro-inflammatory signals converge on the canonical IkB kinase complex (IKK), a protein complex that is composed of two kinases subunits, IKKα/IKK-1 and IKKβ/IKK-2 and a structural/regulatory subunit NEMO/IKK-γ. Once activated IKK complex phosphorylates IkB proteins, triggering their ubiquitination and subsequent degradation by proteasome. Free NF-κB can then move into nucleus to initiate or up-regulate gene expression. Although IKKα and IKKβ exhibit striking structural similarity (52%), exquisite genetic studies have shown that they are involved in two pathways for the activation of NF-κB (Pomerantz, 2002, Mol Cell). IKKβ is the pro-inflammatory kinase that is responsible of activation of classical NF-κB complexes whereas IKKα in association with NF-κB inducing kinase (NIK) plays essential roles in the non-canonical NF-κB signaling pathway (Senftleben, 2001, Science). IKKα plays also a role in keratinocyte differentiation but this process is independent of its kinase activity (Hu, 2001, Nature).

The NEMO protein (NF-κB essential modulator) plays a key role in the NF-κB pathway activation. The NEMO protein is associated with IKKα and IKKβ protein kinases in a high molecular weight complex called the IKK complex. The IKK kinases are activated by phosphorylation upon an unknown mechanism, which is believed to be a result of NEMO oligomerization (Agou et al., 2004, J. Biol. Chem.). The presence of the NEMO protein underlies IKK activation since NEMO-deficient cells are unable to activate NF-κB in response to many stimuli. NEMO is composed of an N-terminal IKK-binding domain including a large coiled-coil (CC1). The C-terminal domain functions as the regulatory part of the protein, which has often been reported as a binding template to link many upstream signaling molecules or viral proteins (Ghosh, 1998, Annu. Rev. Immunol.; Santoro, 2003, EMBO J.) Interestingly, mutations responsible for IP and EDA-ID pathologies were mainly found in this part of the molecules (Döffinger, 2001, Nature Gen.; Zonana, 2000, Am. J. Hum. Genet.). The C-terminal domain is composed of the minimal oligomerization domain including two sucessives coiled-coil motifs, CC2 (residues 246-286) and LZ (residues 390-412) (Tegethoff, 2003, Mol. Cell Biol.; Agou et al., 2004, J. Biol. Chem.), and a zinc finger motif at the extremity of the C-terminus.

The biochemical mechanisms triggering the activation of IKK in response to pro-inflammatory stimuli remain unclear. It has been demonstrated that phosphorylation on two serine residues in the activation T-loop induces activation of the IKKβ. However, the mechanism that leads to this phosphorylation event is still unknown. One possible mechanism consists of the conformation change of the kinase induced by NEMO oligomerization (Agou et al., 2004, J. Biol. Chem.). This change of the oligomeric state may induce the T-loop activation by a mechanism of trans-auto-phosphorylation (Zandi, 1997, Cell; Tang, 2003, J. Biol. Chem.). Consistent with the role of NEMO oligomerization in IKK activation, mutations in the minimal oligomerization domain failed to rescue NF-κB by genetic complementation in NEMO-deficient cells activation in responses to many stimuli. Moreover, enforced oligomerization of NEMO lead to full activation of IKK complex. (Inohara, 2000, J. Biol. Chem.; Poyet, 2000, J. Biol. Chem.; Poyet, 2001, J. Biol. Chem.). Recently, the phosphorylation and the ubiquitination of NEMO in response to TNF-α have been reported, (Carter, 2001, J. Biol. Chem.; Trompouky, 2003, Nature; Kovalenko, 2003, Nature). However, these NEMO modifications have not been demonstrated yet as a crucial step to activate IKK complex in response to several pro-inflammatory stimuli.

Inhibition of NF-κB activation constitutes a privileged target for development of new anti-inflammatory and anti-cancer drugs (May, 2000, Science; Poulaki, 2002, Am J Pathol.). Among many protein actors in NF-κB signaling pathway, IKK complex represents one of the most promising molecular targets for discoveries of the new specific NF-κB inhibitors. To minimize the potential toxicity effects in vivo, therapeutical success will greatly depend on the abilities of the NF-κB inhibitors to block activating signals without modifying the basal level of NF-κB activity. May et al. described a cell-permeable peptidic inhibitor that block specifically the pro-inflammatory NF-κB activation by disrupting the constitutive NEMO interaction with IKK kinases (May, 2000, Science; May, 2002, J. Biol. Chem.). Modulating protein-protein interactions by the rational design of peptide that alter protein's function provides an important tool for both basic research and development of new classes of therapeutic drugs (Souroujon, 1998, Nat Biotechnol.), especially with signaling proteins that exhibit flexible and dynamic binding properties (Pawson, 2003, Science). Numerous studies of peptide modulators have been described in the literature where peptides mediate protein's function by interfering with localization (translocation) (Lin, 1995, J. Biol. Chem.), recruitment to receptor (Chang, 2000, J. Biol. Chem.), intramolecular interactions (Souroujon, 1998, Nat Biotechnol.) and oligomerization (Judice, 1997, P.N.A.S.). In the latter, inhibition of HIV-1 gp41 fusion protein with various peptides provides a clear proof-of concept (for a review see Chan, 1998, Cell and Eckert, 2001, Ann. Rev. Biochem.).

Under this theory that inhibition of NF-κB activation provides a desirable target for the development of new anti-inflammatory and anti-cancer drugs, the present inventors have set forth to discover candidate anti-inflammatory and anti-cancer drugs, as well as to provide a method of screening for the same.

It is an object of the present invention to provide polypeptides derived from NEMO that are useful for the regulation and/or inhibition of the NF-κB signaling pathway.

To this end, the present invention provides NEMO-derived poly-peptides that inhibit the NF-κB signaling pathway.

In one embodiment of the present invention, the NEMO-derived polypeptide is the CC2 domain (murine: SEQ ID NO: 3 or human: SEQ ID NO: 14).

In another embodiment of the present invention, the NEMO-derived polypeptide is the LZ domain (murine: SEQ ID NO: 7 or human: SEQ ID NO: 16).

In a preferred embodiment of the present invention, the NEMO-derived polypeptides are fused via a spacer sequence to a polypeptide having a high transduction potential.

Further, in another embodiment of the present invention are polynucleotides that encode for the NEMO-derived polypeptides either with or without the spacer sequence and the polypeptide having a high transduction potential.

In yet another embodiment of the present invention is methods of modulating or treating disorders regulated by the NF-κB signaling pathway by administering the NEMO-derived polypeptides to a subject in need thereof. The disorders regulated by the NF-κB signaling pathway include: inflammatory responses, oncogenesis, and viral infection.

The present invention also provides a method of regulating cell proliferation or apoptosis by administering the NEMO-derived polypeptides to a subject in need thereof.

In still another embodiment of the present invention is a method of regulating B or T lymphocytes in antigenic stimulation by administering the NEMO-derived polypeptides to a subject in need thereof.

In yet another embodiment, the present invention further provides a method of identifying polypeptides that modulate oligomerization of NEMO by a) identifying a candidate polypeptide sequence;

b) creating a polypeptide fusion construct by linking said candidate polypeptide sequence to a polypeptide having a high transduction potential via a spacer sequence;

c) contacting a cell culture with the polypeptide fusion construct; and d) monitoring the activity of the NF-κB signaling pathway;

e) comparing the activity of the NF-κB signaling pathway in the presence of said polypeptide fusion construct to the activity of the NF-κB signaling pathway in the absence of said polypeptide fusion construct to determine the relative inhibition by said polypeptide fusion construct; and f) correlating relative inhibition by said polypeptide fusion construct to NEMO oligomerization.

The above objects highlight certain aspects of the invention. Additional objects, aspects and embodiments of the invention are found in the following detailed description of the invention.

A more complete appreciation of the invention and many of the attendant advantages thereof will be readily obtained as the same becomes better understood by reference to the following Figures in conjunction with the detailed description below.

FIG. 1: Functional Domains of the NEMO Protein. (A) The murine NEMO protein contains 412 amino acids and multiple domains including the N-terminal IKK binding domain and the oligomerization domain, the proline rich motif (PPP) and the zinc finger motif (ZF) at the C-terminus. The coiled-coil predictions (open boxes) using the algorithm developed by Wolf et al. (1997, Protein Sci.) and the NLM conserved motif (black bar) is shown. The sequence of NEMO$_{253-337}$ (residues 253-337 of SEQ ID NO: 12) corresponding to the second coiled-coil (CC2) and leucine zipper (LZ) motifs, which contains all determinants required for NEMO oligomerization (Agou et al., 2004, J. Biol. Chem.), is indicated with the NLM conserved motif (residues 293-322 of SEQ ID NO: 12) underlined and with the coiled-coil sequences showed as cylinders below the sequence. Letters immediately above the sequence indicate the heptad repeat 'a' and 'd' positions which is a key feature of coiled-coil sequences (Vinson, 2002, Mol. Cell. Biol.). (B) Multiple sequence alignment of NEMO proteins from *Mus musculus* (Mm), *Homo sapiens* (Hs), *Bos taurus* (At) and *Drosophila melanogaster* (Dm), showing the NEMO like motif (NLM) shared with NRP/optineurin, ABIN-1/Naf 1, ABIN-2 and ABIN-3/LIND of different species (SEQ ID NOs:19-29, respectively). The multiple sequence alignment was constructed by parsing PSI-BLAST-generated highest-scoring pairs of sequence segments and realigning the same using with CLUSTAL W (Thompson, 1994, N.A.R.). Identical and similar amino acid residues (shaded) are indicated by (!) or (*), respectively.

Figure 2:
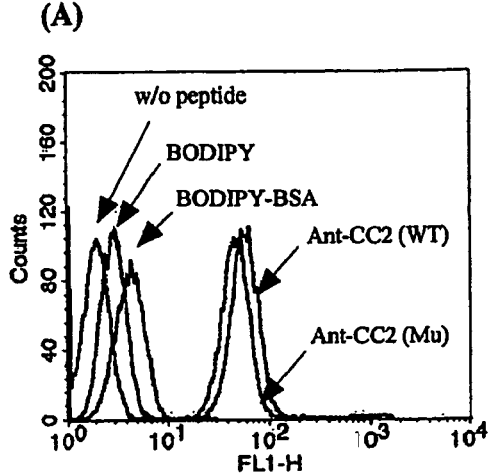
Figure 2:
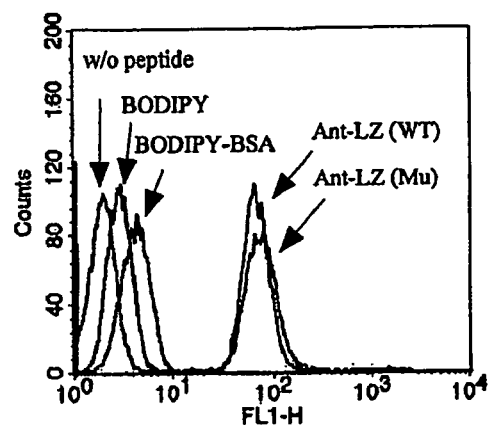
Figure 2:
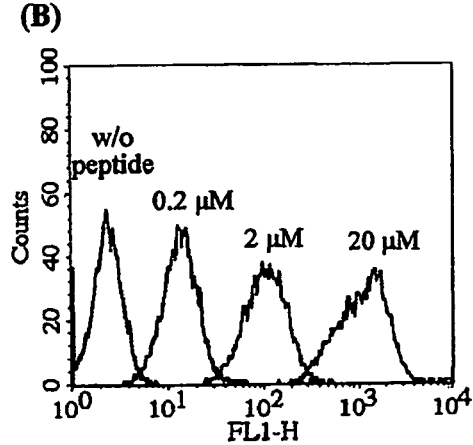
Figure 2:
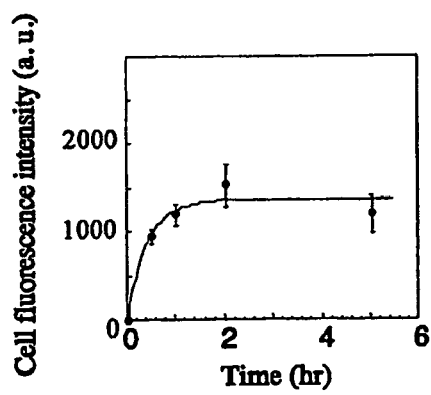

FIG. 2: Flow Cytometry Analysis of NEMO Peptide Uptake (A) Cellular delivery of NEMO peptides mediated by conjugation with the Antennapedia peptide. 70Z/3 cells were incubated for 2 h at 37° C. in the absence (W/O) or in the presence of 2 μM BODIPY-tagged Ant-CC2 wild type (WT), or Ant-CC2 mutant (Mu), or Ant-LZ wild type (WT) or Ant-LZ mutant (Mu) peptide as indicated, or with controls corresponding to 2 μM BODIPY-conjugated BSA (BODIPY-BSA) or BODIPY-FL alone. (B) Concentration dependence of antennapedia-mediated uptake of 0, 0.2, 2 and 20 μM Ant-CC2 at 37° C. for 5 h in 70Z/3-C3 cells (left panel) and FACS kinetic analysis of BODIPY-conjugated Ant-CC2 at 0, 0.5, 1, 2 or 5 h after addition of 20 μM Ant-CC2 at 37° C.

Figure 3:
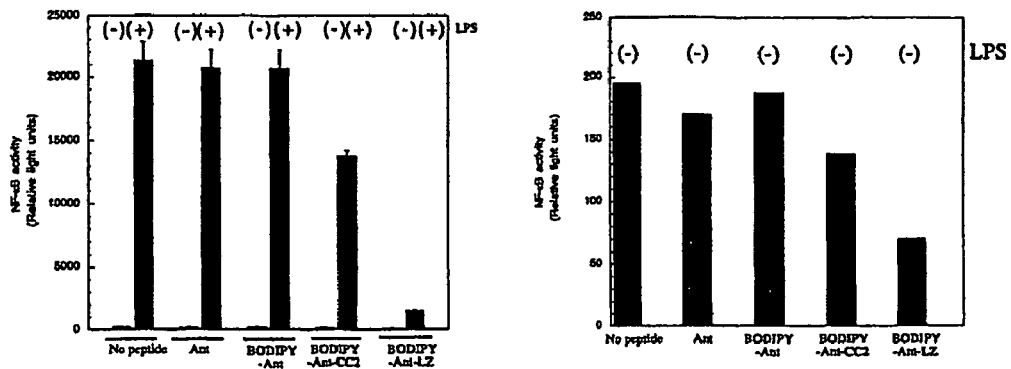
Figure 3:
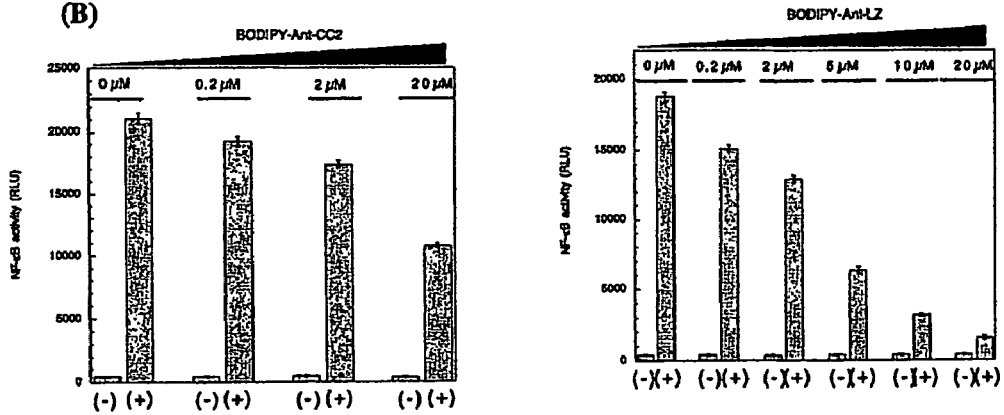
Figure 3:
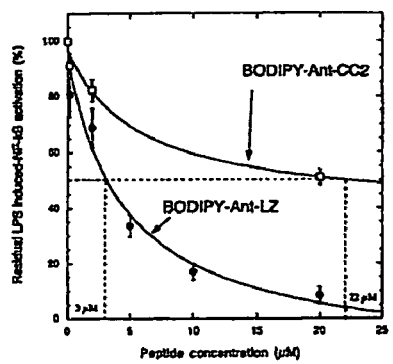
Figure 3:
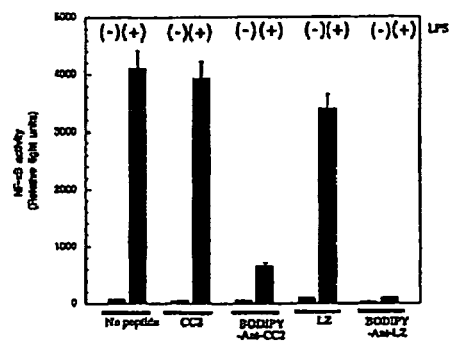

FIG. 3: Inhibition of LPS-Induced NF-κB Activation by Cell-Permeable Ant-CC2 and Ant-LZ Peptide (A) 70Z3 lymphocyte B were stably transfected with pIL1-β-galactosidase, which bears the β-galactosidase gene under the control of the NF-κB (see "Materials and methods"). The resulting cell line, 70Z3-C3, was incubated for 2 hours in the absence or in the presence of 20 μM of antennapedia peptide (Ant), or BODIPY-labeled antennapedia peptide (BODIPY-Ant), or BODIPY-labeled antennapedia peptide coupled to CC2 (BODIPY-Ant-CC2) or LZ (BODIPY-Ant-LZ) peptides, After peptide internalization, cells were treated for 5 hours with LPS (3 μg/ml, (+) in left panel) or untreated (right panel and (−) in left panel) and the NF-κB activity was measured by β-galactosidase assay. Error bars represent the standard deviation of three separate experiments. (B) Concentration dependence of inhibition of LPS-induced NF-κB activation by BODIPY-Ant-CC2 peptide (left panel) or BODIPY-Ant-LZ peptide (right panel). Cells were treated as in (A) but with different concentration of peptide as indicated. The potential of each peptide to inhibit LPS-induced NF-κB activation was measured by determining the IC$_{50}$ value that correspond to 50% inhibition of LPS-induced NF-κB activation as compared to the control (no peptide) (C). (D) Effect of the N-fusion sequence of antennapedia on the inhibition of NF-κB activation. Control (no peptide) or CC2, or LZ peptides, with (BODIPY-ANT-CC2, BODIPY-ANT-LZ) or without the antennapedia sequence at the N-terminus (CC2, LZ) were incubated for 2 hours with 70Z3-C3 cells followed with (+) or without (−) the LPS-treatment for 3 hours. NF-κB activity was then measured by β-galactosidase assay.

Figure 4:
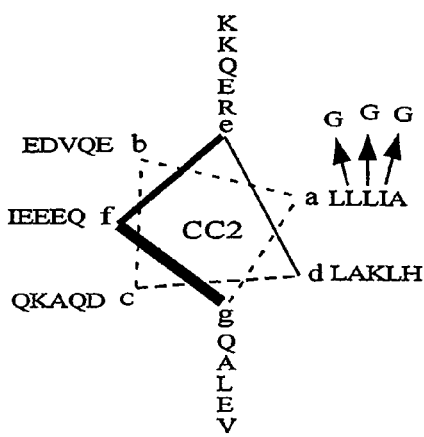
Figure 4:
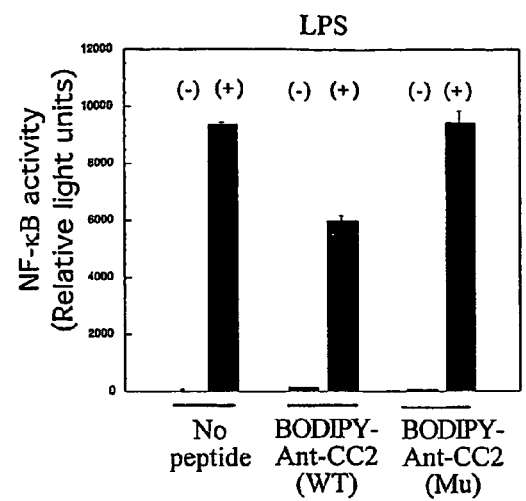
Figure 4:
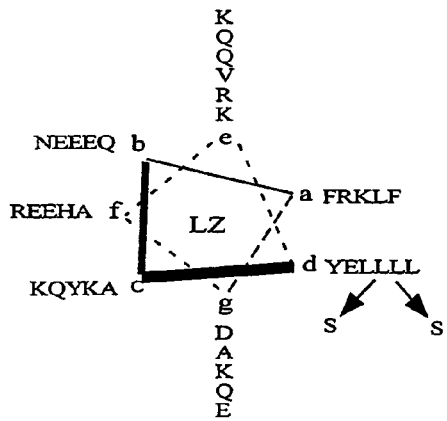
Figure 4:
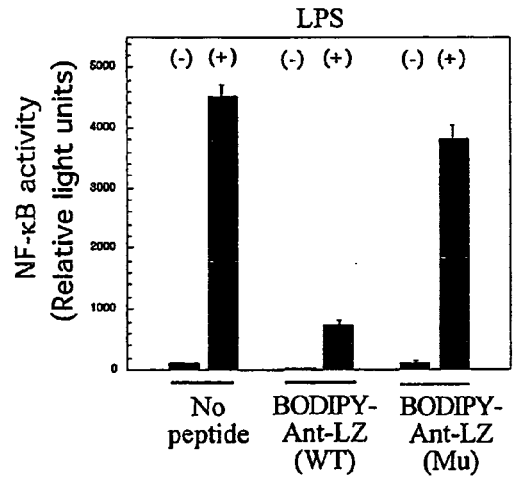

FIG. 4: Specific Inhibition of NF-κB Activation in Response to LPS Depends on a Few Mutations in the Hydrophobic Core of CC2 and LZ Coiled-Coils Left panels show a helical wheel diagram of CC2 (A) and LZ (B) peptides. The view is from the top the molecule. The (a) through (g) positions, which are an essential feature of coiled coil sequence (Vinson, 2002, Mol. Cell. Biol.) represent sequential positions in each peptide sequence. The first (a) and fourth (d) positions that are generally occupied by hydrophobic amino acids constitute the hydrophobic core for parallel as well as antiparallel-coiled coils. Mutations that were introduced in (a) positions of the CC2 variant (BODIPY-Ant-CC2 (Mu); shown as residues 6-40 of SEQ ID NO:3, with glycine mutations corresponding to residues 6-40 of SEQ ID NO:5) or in (d) positions of the LZ variant (BODIPY-Ant-(Mu) are shown. In the right panels, 70Z3-C3 cells were incubated for 2 hours in the absence (control) or in the presence of 10 μM of cell permeable wild type (BODIPY-Ant-CC2 (WT)) or mutant (BODIPY-Ant-CC2 (Mu)) CC2 peptides (A) or wild type (BODIPY-Ant-LZ (WT)) or mutant (BODIPY-Ant-(Mu)) LZ peptides (B). The cells were then extensively washed to remove the excess peptide which had not been internalized and the cells were then diluted three times and allowed to grow for 24 hours before treatment for 5 hours with (+) or without LPS (−). NF-κB activity was measured using the β-galactosidase assay. Error bars represent the standard deviation of two independent experiments.

Figure 5:
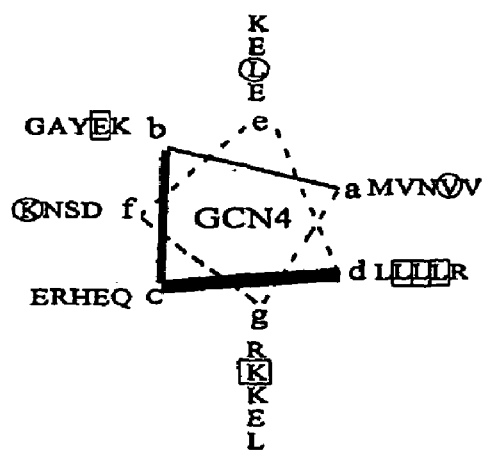
Figure 5:
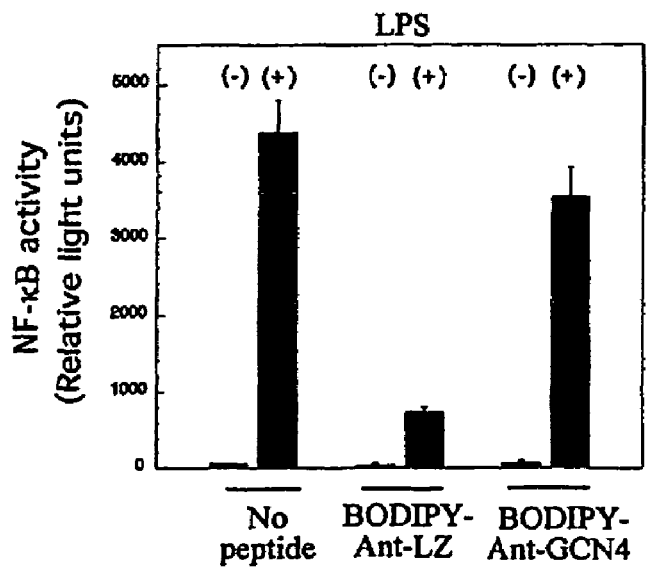

FIG. 5: Inhibition of NF-κB Activation by the LZ Peptide Occurs Through the Formation of Specific Coiled-Coil Strands. (A) Sequence alignment of the NEMO-derived LZ (residues 301-336 of SEQ ID NO:12) and the GCN4 peptides (residues 23-55 of SEQ ID NO:8). Both coiled-coil motifs were aligned using clustalX. Identical and similar amino acid residues (shaded) are indicated by (!) or (*), respectively. Overview and helical wheel diagram of the GCN4 coiled-coil (top view). The amino-acid sequence of GCN4 is shown with its corresponding [a-g] positions and residues that differ from the corresponding NEMO-derived LZ sequence are boxed according to their degree of conservation. Identical (open square) and similar residues (open triangle) are indicated. (B) Comparison of the cell permeable NEMO-derived LZ and GCN4 peptide on the inhibition of LPS-induced NF-κB activation. 70Z3-C3 cells were incubated for 2 hours in the absence (no peptide) or in the presence of 10 μM of the antennapedia fusion LZ (BODIPY-Ant-LZ) or GCN4 (BODIPY-Ant-GCN4) peptide. Cells were then extensively washed to remove any peptide excess which was not internalized, and diluted three times to facilitate 24 hours of growth before treatment for 5 hours with (+) or without LPS (−). NF-κB activity was measured using the β-galactosidase assay. Error bars represent the standard deviation of two independent experiments.

Figure 6:
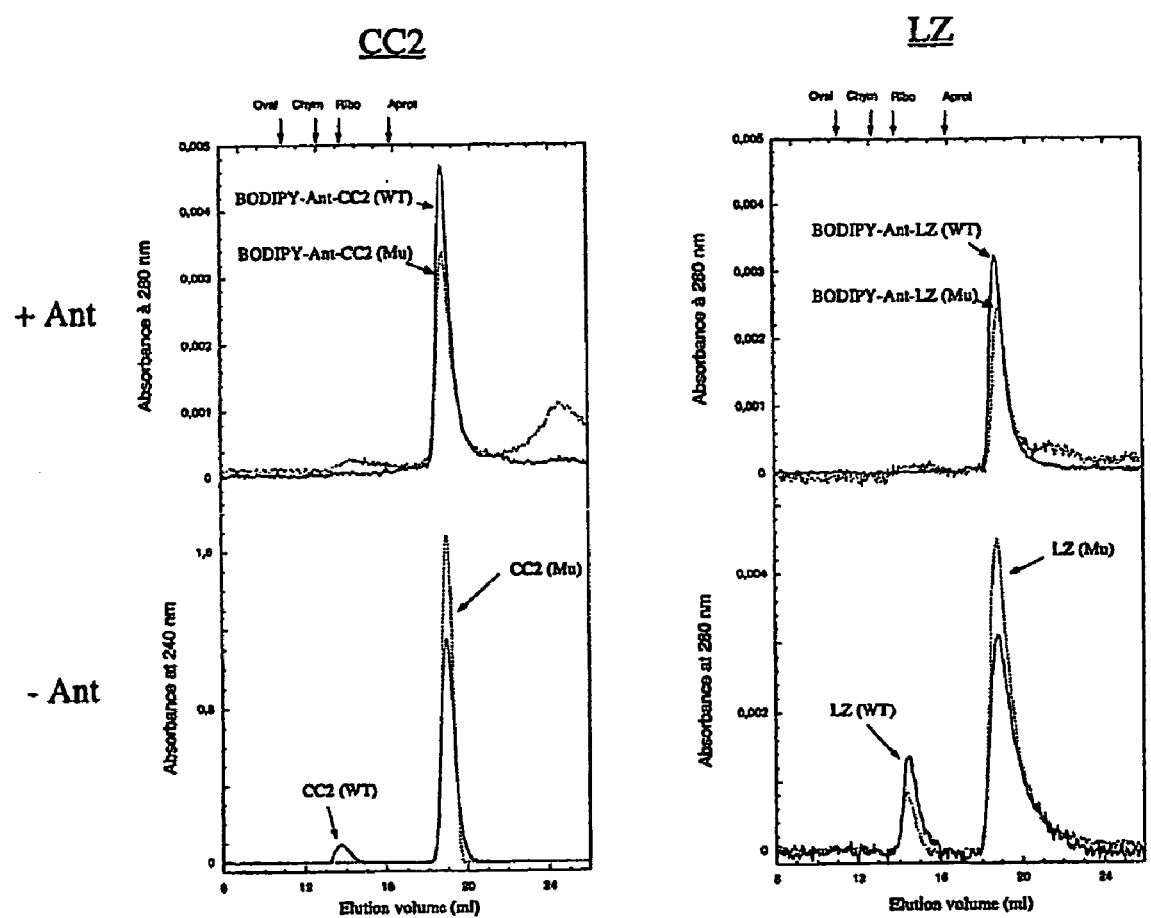

FIG. 6: Oligomerization Properties of NEMO-Derived Polypeptides with or without the Antennapedia Sequence All peptides were loaded at a 10 μM concentration on a superdex 75 HR10/30 column equilibrated in a buffer containing 0.1 mM DDM to improve recovery (see "Materials and methods"). Chromatographic profiles of the CC2 mutant (dashed line) and the CC2 wild type (solid line) fused (BODIPY-Ant-CC2 (WT), BODIPY-Ant-CC2 (Mu), or not fused to the antennapedia sequence (CC2 (WT), CC2 (Mu)) are shown in left panels, and elution profiles of the LZ mutant (dashed line) and the wild type (solid line) fused (BODIPY-Ant-LZ (WT), BODIPY-Ant-LZ (Mu), or not fused to the antennapedia sequence (LZ (WT), LZ (Mu)) are represented in right panels. Elution volumes of globular protein markers are indicated by arrows: Oval, ovalbumin (43 kDa); Chym, chymotrypsinogene A (25 kDa); Ribo, Ribonuclease (13.4 kDa) and Apro, aprotinin (6.5 kDa).

Figure 7:
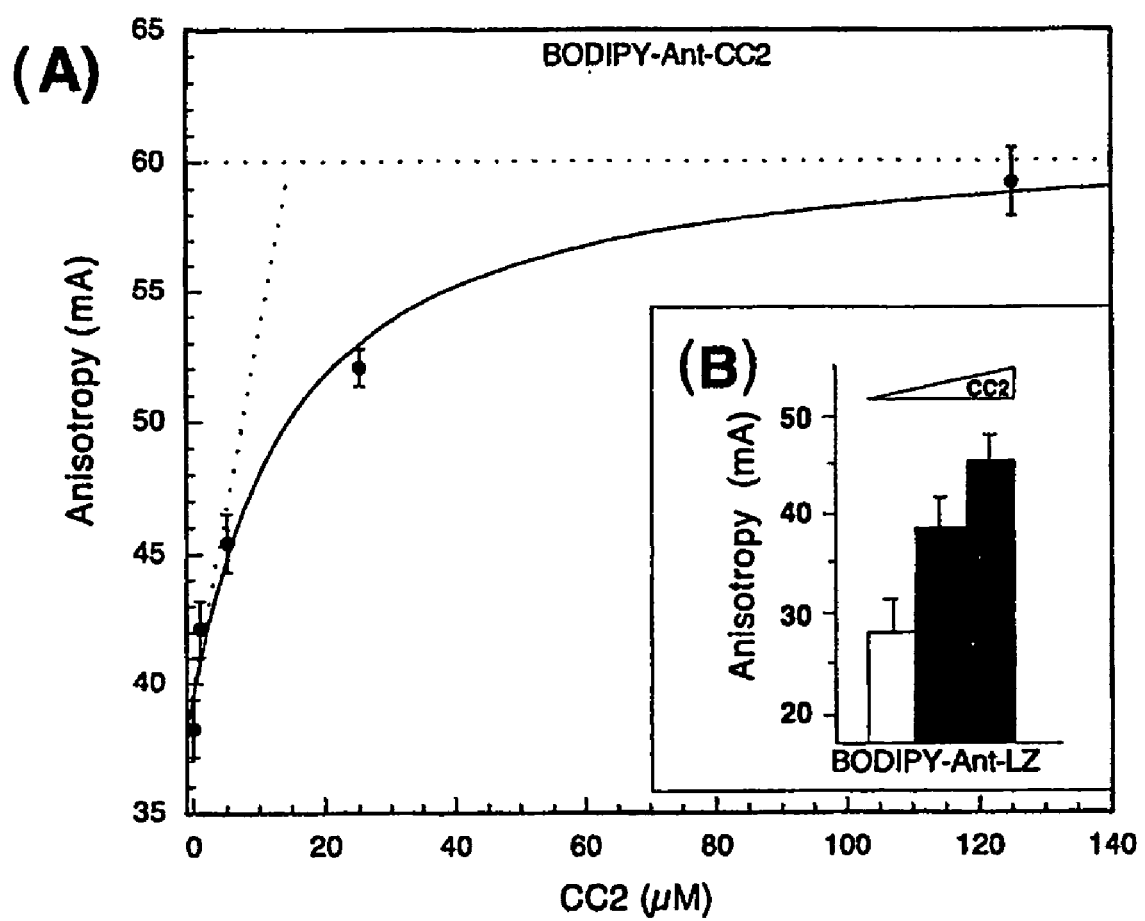

FIG. 7: Association of Ant-CC2 and Ant-LZ Peptides to the CC2 Peptide (A) Direct titration of BODIPY-Ant-CC2 (1 μM) with CC2 by fluorescence anitropy. The concentration of CC2 was determined by amino acid analysis. Anisotropy values of BODIPY-Ant-CC2 in milliunits (mA) were plotted against an increasing concentration of the CC2 peptide. Data points were fitted (solid line) to the binding isotherm equation with a $K_D$ of 15.2 μM (Materials and Methods). The two dashed lines represent a stoichiometric titration and intersect at an CC2 concentration of 16 μM. Given the 1 μM concentration of the BODIPY-Ant-CC2, this gives a complex stoechiometrie of 0.8. (B) Direct titration of BODIPY-Ant-LZ (0.1 μM with CC2 by fluorescence anitropy. The anisotropy values of the BODIPY-Ant-LZ alone (white bar) or in the presence of the CC2 peptide (30 μM, grey bar; 100 μM, black bar) are given in milliunits (mA).

Figure 8:
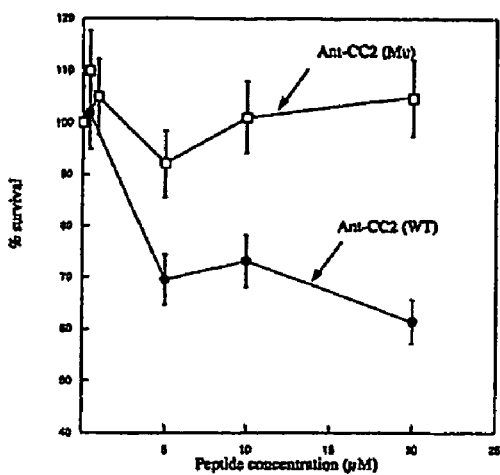
Figure 8:
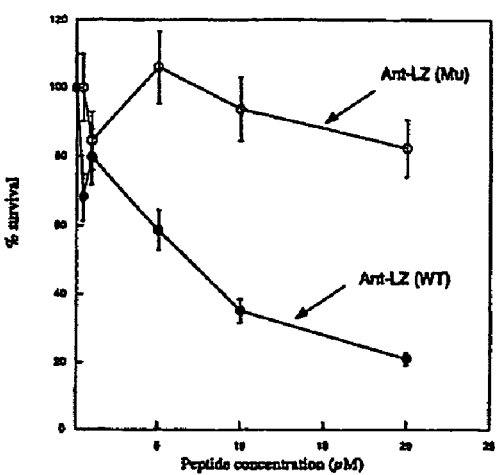
Figure 8:
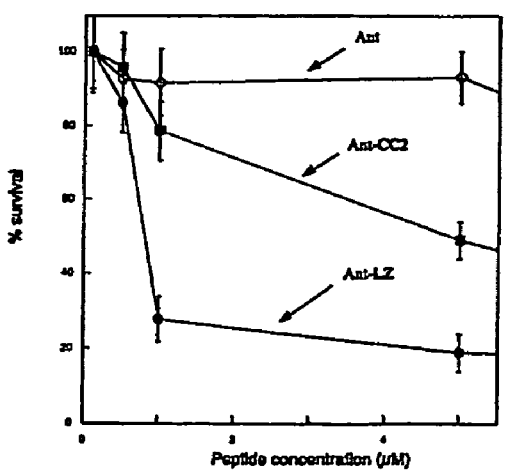

FIG. 8: Cell Death Induced in the Retinoblastoma Cell Line Y79 by Ant-CC2 and Ant-LZ Peptides Rb cell line Y79 were treated with various concentration of the Ant-CC2 (WT) (filled squares) or Ant-CC2 (Mu) (open squares) (A), or Ant-LZ (WT) (filled circles), or Ant-LZ (Mu) (open circles) (B), or Ant peptide (open triangle) (C) for 3 hours (A, B) or 16 hours (C). Cell survival was then evaluated using the MTS assay as described in "Materials and methods"

Unless specifically defined, all technical and scientific terms used herein have the same meaning as commonly understood by a skilled artisan in enzymology, biochemistry, cellular biology, molecular biology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

In this application, the present inventors studied the inhibition of NF-κB activation by peptides designed to disrupt NEMO oligomerization. The present inventors have previously shown that the minimal trimerization domain comprises the CC2-LZ coiled-coil subdomain and that the isolated and/or purified CC2 and LZ domains bind to each other to form a stable trimer of heterodimers. This structural model is reminiscent of the fold of the gp41 ectodomain from HIV-1 (Agou et al., 2004, J. Biol. Chem.). It consist of a central three-stranded coiled coil (formed by the CC2 coiled coil motif of NEMO) which is surrounded by the LZ helical motif derived from the C-terminal end of NEMO, packed in an antiparallel manner around the outside of the CC2 coiled-coil. On the basis of this model, the present inventors rationally designed two cell-permeable peptides corresponding to optimal portions of CC2 or LZ subdomains that mimic the contact area between NEMO subunits. Peptide transduction was monitored by FACS and their effect on LPS-induced NF-κB activation was quantified using a NF-κB dependent β-galactosidase assay in stably transfected pre-B 70Z/3 lymphocytes. The present inventors have also demonstrated that the LZ peptide and, to a lesser extent the CC2 peptide, inhibit specifically NF-κB activation with $IC_{50}$ values in the μM range. The effects were specific because control peptides including mutated CC2 and LZ peptides as well as heterologous coiled-coil peptides (GCN4), had no inhibitory effect on NF-κB activation. Furthermore, the present inventors have shown that these NF-κB peptidic inhibitors induced the cell death in the human retinoblastoma cell lines Y79 that exhibit constitutive NF-κB activity. Collectively, the present inventors have provided a new and promising strategy to inhibit the NF-κB pathway by targeting NEMO's oligomerization.

The present inventors have proven that NEMO constitutes a preferential target for the search for drugs inhibiting the NF-κB signaling path, because this protein acts upstream from the NF-κB activation path. The role of NEMO and its various domains was partially studied and published in the following article, *"NEMO trimerizes through its coiled-coil C-terminal domain."* J Biol Chem, 2002 May 17; 277(20): 17464-75. Agou F. et al., a copy of which is incorporated by reference.

In the present invention, the inventors have synthesized peptides that mimic either the oligomerization domain (CC2 domain=approx. 40 residues), or the LZ motif (LZ domain=approx. 40 residues). The combination of these peptides alters either the oligomerization of NEMO or the combining thereof with the proteinic effector, in both cases inhibiting the NF-κB pathway.

In an aspect of the present invention, peptide drugs have been chemically combined with a peptide of 16 amino acids in length (penetratin/antennapedia), thereby enabling intracellular transport thereof possible. The resulting peptides also may be chemically coupled with a fluorescent tracer in order to monitor internalization into B lymphocyte cell lines through FACS.

The action of these peptides was tested directly on B lymphocytes having stably integrated the beta-galactosidase carrier gene also bearing upstream from its promoter several NF-κB transcription factor (Clone C3) activation sites (see Examples herein below).

The present inventors have successfully been able to monitor the inhibitory effect of these peptides by measuring the same following stimulation of the B lymphocytes by LPS.

The results as a whole reveal that the presence of the peptide mimicking the "CC2" motif reduces the NF-κB activity by 70% as compared with a control peptide at a relatively low dose of 20 μM. At this concentration, the effect of the "Leucine zipper" peptide is still more significant, since its presence in the medium completely eliminates cell response.

These new inhibitors of the NF-κB cellular signalling path offer a major advantage as anti-inflammatory compounds and also as anti-tumor compounds, which may be used for the treatment and/or prevention of cancers and other disorders.

The present invention relates to compounds, peptides, or compositions that are used for modulating the oligomerization of NEMO. In particular, the peptide compounds described herein below may be in an isolated and/or purified or coupled form with or without a vectorizing agent. It is to be understood that the present invention also embraces peptides having at least 70% homology with the NEMO-derived polypeptides, so long as the homologs possess said inhibitory activity. Methods for assessing inhibitory activity of the NEMO-derived polypeptides, and homologs thereof, are provided below and exemplified in the Examples of the present application. The peptides of the present invention and the doses thereof are deemed to possess inhibitory activity when the NF-κB activity is reduced by at least 50% as compared with a control peptide.

The present invention also relates to pharmaceutical compositions containing said peptides, especially for the preparation of medicines used for the treatment of inflammatory responses, oncogenesis, viral infection, the regulation of cell proliferation and apoptosis and antigenic stimulation. In a preferred embodiment, the pharmaceutical compositions containing said peptides are useful for the treatment of cancer.

Also embraced by the present invention are methods of obtaining, making, and identifying peptides and compounds that inhibit the NF-κB signaling pathway, in particular by means of the 70Z/3-C3 cell line filed with the CNCM (Collection Nationale de Cultures de Microorganismes), 28 rue du Docteur Roux, 75724 PARIS Cedex 15, France, on Apr. 1, 2003 under number I-3004.

As used herein, the term "reduced" or "inhibited" means decreasing the intracellular activity of one or more enzymes in the NF-κB pathway either directly or indirectly. The phrase "inhibiting the NF-κB pathway" preferably means that the NF-κB pathway is inhibited by disruption of NEMO oligomerization.

The term "enhanced" as used herein means increasing the intra-cellular activity or concentration of the NEMO derived peptides, which are encoded by the corresponding DNA. Enhancement can be achieved with the aid of various manipulations of the bacterial cell. In order to achieve enhancement, particularly over-expression, the number of copies of the corresponding gene can be increased, a strong promoter can be used, or the promoter- and regulation region or the ribosome binding site which is situated upstream of the structural gene can be mutated. Expression cassettes which are incorporated upstream of the structural gene act in the same manner. In addition, it is possible to increase expression by employing inducible promoters. A gene can also be used which encodes a corresponding enzyme with a high activity. Expression can also be improved by measures for extending the life of the mRNA. Furthermore, preventing the degradation of the enzyme increases enzyme activity as a whole. Moreover, these measures can optionally be combined in any desired manner. These and other methods for altering gene activity in a plant are known as described, for example, in Methods in Plant Molecular Biology, Maliga et al, Eds., Cold Spring Harbor Laboratory Press, New York (1995).

A gene can also be used which encodes a corresponding or variant NEMO derived peptide with a high activity of inhibiting the NF-κB pathway. Preferably the corresponding enzyme has a greater ability than the native form of the NEMO protein to inhibit the NF-κB pathway, more preferably at least in the range of 5, 10, 25% or 50% more inhibition. Most preferably the NEMO derived peptides of the present invention reduce the NF-κB pathway by at least 50%, at least 75%, at least 80%, at least 85%, at least 90%, at least 95%, as compared to the pathway in the presence of the native NEMO protein.

In the context of the present Application, a polynucleotide sequence is "homologous" with the sequence according to the invention if at least 70%, preferably at least 80%, most preferably at least 90% of its base composition and base sequence corresponds to the sequence according to the invention. According to the invention, a "homologous protein" or "homologous peptide" is to be understood to comprise proteins (peptides) which contain an amino acid sequence at least 70% of which, preferably at least 80% of which, most preferably at least 90% of which, corresponds to the amino acid sequence of the CC2 region of NEMO (SEQ ID NO: 3) or the LZ region of NEMO (SEQ ID NO: 7) in the case of murine-derived NEMO and the CC2 region of NEMO (SEQ ID NO: 14) or the LZ region of NEMO (SEQ ID NO: 16) in the case of human-derived NEMO, wherein corresponds is to be understood to mean that the corresponding amino acids are either identical or are mutually homologous amino acids. It is further to be understood that, as evinced by the Examples of the present invention, the homologous peptide of CC2 preferably retains the coiled-coil motif structure and the homologous peptide of LZ preferably retains the helical motif structure. With the guidance proffered by the identification of SEQ ID NO: 3, SEQ ID NO: 7, SEQ ID NO: 14, and SEQ ID NO: 16 and the detailed description in the Examples below, screening of theoretical mutations within the scope of the present invention would require nothing more than a technicians level of skill in the art. More specifically, as is routine in the art, with the identification of a candidate sequence (i.e., the regions corresponding to SEQ ID NO: 3, SEQ ID NO: 7, SEQ ID NO: 14, and SEQ ID NO: 16) the artisan would assay and screen one or all possible permutations of the said sequence to identify mutants possessing the same or better therapeutic efficacy.

The expression "homologous amino acids" denotes those that have corresponding properties, particularly with regard to their charge, hydrophobic character, steric properties, etc.

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482-489 (1981), to find the best segment of identity or similarity between two sequences. Gap performs global alignments: all of one sequence with all of another similar sequence using the method of Needleman and Wunsch, J. Mol. Biol. 48:443-453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

The present invention also relates to polynucleotides which encode the CC2 region of NEMO (SEQ ID NO: 3) or the LZ region of NEMO (SEQ ID NO: 7) in the case of murine-derived NEMO and the CC2 region of NEMO (SEQ ID NO: 14) or the LZ region of NEMO (SEQ ID NO: 16) in the case of human-derived NEMO, or fragments thereof, and which can be obtained by screening by means of the hybridization of a corresponding gene bank with a probe which contains the sequence of said polynucleotide that encodes the CC2 region of NEMO (SEQ ID NO: 3) or the LZ region of NEMO (SEQ ID NO: 7) in the case of murine-derived NEMO and the CC2 region of NEMO (SEQ ID NO: 14) or the LZ region of NEMO (SEQ ID NO: 16) in the case of human-derived NEMO, or fragments thereof, and isolation of said DNA sequence.

Polynucleotide sequences according to the invention are suitable as hybridization probes for RNA, cDNA and DNA, in order to isolate those cDNAs or genes that exhibit a high degree of similarity to the sequence that encodes the CC2 region of NEMO (SEQ ID NO: 3) or the LZ region of NEMO (SEQ ID NO: 7) in the case of murine-derived NEMO and the CC2 region of NEMO (SEQ ID NO: 14) or the LZ region of NEMO (SEQ ID NO: 16) in the case of human-derived NEMO, or fragments thereof.

Polynucleotide sequences according to the invention are also suitable as primers for polymerase chain reaction (PCR) for the production of DNA, which encodes a NEMO-derived polypeptide having an ability to inhibit the NF-κB pathway.

Oligonucleotides such as these, which serve as probes or primers, can contain more than 30, preferably up to 30, more preferably up to 20, most preferably at least 15 successive nucleotides. Oligonucleotides with a length of at least 40 or 50 nucleotides are also suitable.

The term "isolated and/or purified" means separated from its natural environment.

The term "polynucleotide" refers in general to polyribonucleotides and polydeoxyribonucleotides, and can denote an unmodified RNA or DNA or a modified RNA or DNA.

The term "polypeptides" is to be understood to mean peptides or proteins that contain two or more amino acids that are bound via peptide bonds.

The polypeptides according to invention include polypeptides corresponding to the CC2 region of NEMO (SEQ ID NO: 3) or the LZ region of NEMO (SEQ ID NO: 7) in the case of murine-derived NEMO and the CC2 region of NEMO (SEQ ID NO: 14) or the LZ region of NEMO (SEQ ID NO: 16) in the case of human-derived NEMO, or fragments thereof, particularly those with the biological activity of inhibition the NF-κB pathway, and also includes those, at least 70% of which, preferably at least 80% of which, are homologous with the polypeptide corresponding to the CC2 region of NEMO (SEQ ID NO: 3) or the LZ region of NEMO (SEQ ID NO: 7) in the case of murine-derived NEMO and the CC2 region of NEMO (SEQ ID NO: 14) or the LZ region of NEMO (SEQ ID NO: 16) in the case of human-derived NEMO, or fragments thereof, and most preferably those which exhibit a homology of at least 90% to 95% with the polypeptide corresponding to the CC2 region of NEMO (SEQ ID NO: 3) or the LZ region of NEMO (SEQ ID NO: 7) in the case of murine-derived NEMO and the CC2 region of NEMO (SEQ ID NO: 14) or the LZ region of NEMO (SEQ ID NO: 16) in the case of human-derived NEMO, or fragments thereof, and which have the cited activity.

The invention also relates to coding DNA sequences that encode the CC2 region of NEMO (SEQ ID NO: 3) or the LZ region of NEMO (SEQ ID NO: 7) in the case of murine-derived NEMO and the CC2 region of NEMO (SEQ ID NO: 14) or the LZ region of NEMO (SEQ ID NO: 16) in the case of human-derived NEMO, or fragments thereof, by degeneration of the genetic code. One of skill in the art would appreciate that the aforementioned DNA sequences may be based on the full-length DNA sequences for the murine-derived NEMO (SEQ ID NO: 11) and the human-derived NEMO (SEQ ID NO: 17) and thereby these sequences may be used to ascertain the scope of these sequences in accordance with the present invention.

In the same manner, the invention further relates to DNA sequences that hybridize with DNA sequences that encode the CC2 region of NEMO (SEQ ID NO: 3) or the LZ region of NEMO (SEQ ID NO: 7) in the case of murine-derived NEMO and the CC2 region of NEMO (SEQ ID NO: 14) or the LZ region of NEMO (SEQ ID NO: 16) in the case of human-derived NEMO, or fragments thereof.

Moreover, one skilled in the art is also aware of conservative amino acid replacements such as the replacement of glycine by alanine or of aspartic acid by glutamic acid in proteins as "sense mutations" which do not result in any fundamental change in the activity of the protein, i.e. which are functionally neutral. It is also known that changes at the N- and/or C-terminus of a protein do not substantially impair the function thereof, and may even stabilize said function.

In the same manner, the present invention also relates to DNA sequences that hybridize with the DNA sequence that encodes the CC2 region of NEMO (SEQ ID NO: 3) or the LZ region of NEMO (SEQ ID NO: 7) in the case of murine-derived NEMO and the CC2 region of NEMO (SEQ ID NO: 14) or the LZ region of NEMO (SEQ ID NO: 16) in the case of human-derived NEMO, or fragments thereof. The present invention also relates to DNA sequences that are produced by polymerase chain reaction (PCR) using oligonucleotide primers that result from the DNA sequence that encodes the CC2 region of NEMO (SEQ ID NO: 3) or the LZ region of NEMO (SEQ ID NO: 7) in the case of murine-derived NEMO and the CC2 region of NEMO (SEQ ID NO: 14) or the LZ region of NEMO (SEQ ID NO: 16) in the case of human-derived NEMO, or fragments thereof. Oligonucleotides of this type typically have a length of at least 15 nucleotides.

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the Tm can be approximated from the equation of Meinkoth and Wahl, Anal. Biochem., 138:267-284 (1984): Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Current Protocols in Molecular Biology, Chapter 2, Ausubel, et al., Eds., Greene Publishing and Wiley-Interscience, New York (2000).

Thus, with the foregoing information, the skilled artisan can identify and isolated and/or purified polynucleotides, which are substantially similar to the present polynucleotides. In so isolating such a polynucleotide, the polynucleotide can be used as the present polynucleotide in, for example, inhibiting the NF-κB pathway.

One embodiment of the present invention is methods of screening for polynucleotides, which have substantial homology to the polynucleotides of the present invention, preferably those polynucleotides encoding a protein having an ability of inhibiting the NF-κB pathway.

The polynucleotide sequences of the present invention can be carried on one or more suitable plasmid vectors, as known in the art for plants or the like.

In one embodiment, it may be advantageous for propagating the polynucleotide to carry it in a bacterial or fungal strain with the appropriate vector suitable for the cell type. Common methods of propagating polynucleotides and producing proteins in these cell types are known in the art and are described, for example, in Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989).

The aforementioned embodiments are described in the context of SEQ ID NO: 3 (CC2 region of the NEMO protein; i.e., amino acids 246-286 of SEQ ID NO: 12) and SEQ ID NO: 7 (LZ region of the NEMO protein; i.e., amino acids 390-412 of SEQ ID NO: 12), where SEQ ID NO: 12 is murine-derived NEMO. The aforementioned embodiments have been further described based on SEQ ID NO: 14 and SEQ ID NO: 16, which are derived from SEQ ID NO: 18 (human-derived NEMO). However, it is understood that the present invention preferably provides peptide derivatives of the NEMO protein that may be internalized into eukaryotic cells. Internalization of the NEMO peptide derivatives may be imparted by fusing the NEMO peptide derivative(s), or homologues thereof, to a polypeptide having a high transduction potential. The skilled artisan would readily appreciate that the term "high transduction potential" as used herein means that the polypeptide, and the fusion protein thereof, readily transverses the cellular membrane resulting in the internalization of fusion peptide into the cellular milieu. Examples of peptides having a high transduction potential include: the third helix of the Antennapedia/penetratin protein (Ant) (Prochiantz, 2000, Curr. Opin. Cell Biol.), TAT derived peptides (Fawel, 1994, P.N.A.S.), VP22 from HSV-1 (Stroh C. 2003, Oncogene), Pep. 1 (Morris, 2001, Nature Biotech.).

To exemplify the present invention and the utility thereof, the present inventors have fused SEQ ID NO: 3 and SEQ ID NO: 7 to the internalization peptide Ant (SEQ ID NO: 1) separated by a short SKGMQ linker (SEQ ID NO: 9) or by a LKAQADI linker (SEQ ID NO: 10). The resultant Ant-CC2 construct has the sequence: CRQIKIWFQNRRMK-WKKSKGMQLEDLRQQLQQAEEALVAKQELI DKL-KEEAEQHKIV (SEQ ID NO: 2), where the N-terminal cysteine has been added for coupling to a fluorophore to facilitate detection of internalization and/or inhibition. The resultant Ant-LZ construct has the sequence: CRQIKIWFQNRRMK-WKKLKAQADIYKADFQAERHAREK-LVEKKEYLQEQLE QLQREFNKL (SEQ ID NO: 6), where the N-terminal cysteine has been added for coupling to a flurophore to facilitate detection of internalization and/or inhibition.

In the present invention the N-terminal cysteine is an optional addition and, as such, this residue may be omitted from the final inhibitory peptide. Further, in the present invention the linker between the peptide having a high transduction potential (e.g., Ant) and the CC2 or LZ peptide can be of a variable sequence and/or length, so long as the linker sequence does not significantly diminish the inhibitory property of CC2 or LZ peptide. To this end, the linker may be of a length ranging from 1-35 amino acids, preferably 2-25 amino acids, more preferably 3-15 amino acids, most preferably 4-10 amino acids. In a particularly preferred embodiment, the linker sequence is that of SEQ ID NO: 9 or SEQ ID NO: 10.

As set forth hereinabove, it is to be understood that the homologous peptide of CC2 preferably retains the coiled-coil motif structure and the homologous peptide of LZ preferably retains the helical motif structure, even when in the fusion construct set forth above. As such, the present invention embraces homologous peptides, within the homology constraints above, of SEQ ID NO: 2 and SEQ ID NO: 6 (murine-derived) and SEQ ID NO: 13 and SEQ ID NO: 15 human-derived) with the caveat that said homologous peptides retain the structure of CC2 and LZ respectively, as well as the ability to inhibit the NF-κB pathway.

In an embodiment of the present invention, the inventors explored the N-terminal region of the wild-type NEMO, in particular the NLM conserved motif (residues 293-322 of SEQ ID NO: 12) appearing in FIG. 1A. To this end, the following sequences were produced (see Table 1 for the corresponding sequence):

```
NLM-DR          (SEQ ID NO: 30)

Ant.NLM-DR      (SEQ ID NO: 31)

Tat NLM-DR      (SEQ ID NO: 32)

R7-NLM-DR       (SEQ ID NO: 33)

R9-NLM-DR       (SEQ ID NO: 34)
```

NLM-DR is a 21 amino acid "motif" (and the corresponding wild type NLM covering the same amino acid range) derived from the larger 30 amino acid conserved NLM motif set forth in FIG. 1A. The NLM-DR has been mutated from the wild type NLM sequence in that the aspartic acid at residue 11 in the wild type sequence has been replaced by an arginine (see Table 1 and SEQ ID NO: 30). This mutation was selected because, as confirmed by structural studies, the resulting polypeptide would facilitate an intramolecular salt bridge allowing the stabilization of the peptide in its helicoidal form.

From circular dichroism studies (CD), it appears that CC2 and LZ peptides adopt a helicoidal structure, depending on their concentration. CC2 creates a helix more stable than LZ. RMN and Rayon X Diffraction studies have confirmed the structure of CC2. Always, by CD studies, the NLM-DR peptide is structured as a helix more stable than the wild-type peptide.

Although, the polypeptides utilized in this example are 21 amino acids long, it is contemplated in the present invention that the operable size of the NLM fragment may be as short as 15 amino acids. In addition, any mutation in the sequence of the NLM polypeptides that are able to reinforce the helicity and the intermolecular interactions between the peptides and their molecular target would be of particular interest and is within the scope of the present invention.

In the present invention it is speculated that Antennapedia mediated monomerization of peptides may be crucial. Specifically, it is speculated that monomerization allows them to interfere with NEMO oligomerization.

Nuclear factor-kB (NF-κB) signaling is an essential signal transduction pathway involved in inflammatory responses, oncogenesis, viral infection, the regulation of cell proliferation and apoptosis; and in the case of B and T lymphocytes in antigenic stimulation (Ghosh, 1998, Annu. Rev. Immunol.; Karin, 1999, J. Biol. Chem.; Israel, 2000, Trends Cell Biol.; Santoro, 2003, EMBO J.). As such, the inventive peptides are useful for the modulation of and/or treatment of inflammatory responses, oncogenesis, viral infection; the regulation of cell proliferation and apoptosis; and regulation of B or T lymphocytes in antigenic stimulation. Therefore, the present invention provides for a method of treating the same by administering to a subject in need thereof a peptide in accordance with the present invention.

In the present invention, the "subject in need thereof" may be a human, a domestic animal, a farm animal, or an animal that is generally found in the wild. For example, the subject may be selected from a human, a dog, a cat, a horse, a cow, a mouse, a guinea pig, a sheep, a pig, etc.

Clearly, the amount of the peptide to be administered will depend on the subject to which it is to be administered. In the case where the subject is a human, the amount of the peptide to be administered will depend on a number of factors including the age of the patient, the severity of the condition and the past medical history of the patient and always lies within the sound discretion of the administering physician. Generally, the total daily dose of the compounds of this invention administered to a human or other mammal in single or in divided doses can be in amounts, for example, of from 0.1 mg/Kg/day to 30 mg/Kg/day of the peptide, preferably from 0.1 mg/Kg/day to 20 mg/Kg/day of the peptide, more preferably from 2 mg/Kg/day to 10 mg/Kg/day of the peptide, in single or multiple doses. Single dose compositions may contain such amounts or submultiples thereof to make up the daily dose. In a preferred embodiment, the preferred dose is 10 mg/patient to be administered twice a day. In a particularly preferred embodiment, the administration route is intravenous.

The peptides of the present invention may also be administered as a component of a pharmaceutically administrable composition. In other words, the peptide may be present in a formulation for administration to a subject in need thereof. The inventive peptide may be the sole active ingredient for NF-κB pathway inhibition or for treatment of inflammatory responses, oncogenesis, viral infection, the regulation of cell proliferation and apoptosis and antigenic stimulation. Alternatively, the composition may also contain one or more additional compounds that may be used to treat the same. In addition, the peptide of the present invention may be in a composition that contains one or more compounds that are useful for treatment of a disorder not caused by the NF-κB pathway.

A therapeutically effective amount of the peptides suitable for administration in the present invention may be administered alone or in combination with one or more pharmaceutically acceptable carriers. As used herein, the term "pharmaceutically acceptable carrier" means a non-toxic, inert solid, semi-solid or liquid filer, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions suitable for administration in the invention can be administered to humans and other animals orally, rectally, nasally, parenterally (e.g., intramuscular, intraperitoneal, intravenous or subcutaneous injection, or implant), intracisternally, intravaginally, intraperitoneally, sublingually, topically (e.g., as a powder, ointment, or drop), bucally, as an oral spray, or a nasal spray. The pharmaceutical compositions can be formulated in dosage forms appropriate for each route of administration.

Liquid dosage forms for oral administration include pharmaceutically acceptable emulsions, microemulsions, solutions, suspensions, syrups and elixirs. In addition to the active NEMO-derived polypeptides, the liquid dosage forms may contain inert diluents commonly used in the art. The inert diluents may include, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetra-hydrofurfuryl alcohol, polyethylene glycols and fatty acid esters of sorbitan, and mixtures thereof. The liquid dosage form for oral administration may also contain adjuvants, which include wetting agents, emulsifying and suspending agents, sweetening, flavoring, and perfuming agents. Other dosage forms for oral administration include, for example, aqueous suspensions containing the active NEMO-derived polypeptides in an aqueous medium in the presence of a non-toxic suspending agent such as sodium carboxy-methylcellulose, and oily suspensions containing a NEMO-derived polypeptides of the present invention in a suitable vegetable oil, for example arachis oil.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of the inventive NEMO-derived polypeptides, it is often desirable to slow the absorption of the peptides from subcutaneous or intramuscular injection. This may be accomplished by the use of a liquid suspension of crystalline or amorphous material with poor water solubility. The rate of absorption of the NEMO-derived polypeptides then depends upon its rate of dissolution, which, in turn, may depend upon crystal size and crystalline form. Alternatively, dissolving or suspending the drug in an oil vehicle accomplishes delayed absorption of a parenterally administered NEMO-derived polypeptides form. Injectable depot forms are made by forming microencapsulated matrices of the NEMO-derived polypeptides in biodegradable polymers such as polylactide-polyglycolide. Depending upon the ratio of NEMO-derived polypeptides to polymer and the nature of the particular polymer employed, the rate of NEMO-derived polypeptides release can be controlled. Examples of other biodegradable polymers include poly (orthoesters) and poly(anhydrides) Depot injectable formulations are also prepared by entrapping the NEMO-derived polypeptides in liposomes or microemulsions which are compatible with body tissues.

Compositions for rectal or vaginal administration are preferably suppositories which can be prepared by mixing the NEMO-derived polypeptides of this invention with suitable non-irritating excipients or carriers such as cocoa butter, polyethylene glycol or a suppository wax which are solid at ambient temperature but liquid at body temperature and therefore melt in the rectum or vaginal cavity and release the peptide.

Solid dosage forms for oral administration include capsules, tablets, pills, prills, powders, and granules. In such solid dosage forms, the peptide is mixed with at least one inert, pharmaceutically acceptable excipient or carrier. In addition, the solid dosage form may contain one or more fillers, extenders, binders, humectants, disintegrating agents, retarding agents, absorption accelerators, wetting agents, absorbents, or lubricants. Examples of suitable fillers or extenders include, starches, lactose, sucrose, glucose, mannitol, and silicic acid, sodium citrate and dicalcium phosphate. Examples of suitable binders include, microcrystalline cellulose, carboxymethyl-cellulose, alginates, gelatin, polyvinylpyrrolidinone, sucrose, and acacia. Glycerol is an example of a suitable humectant. Examples of suitable disintegrating agents include, agar-agar, calcium carbonate, potato or tapioca starch, maize starch, alginic acid, certain silicates, and sodium carbonate. Paraffin is an example of a suitable solution-retarding agent. As absorption accelerators, any quaternary ammonium compound may be used. Examples of suitable wetting agents include, cetyl alcohol and glycerol monostearate. Examples of suitable absorbents include, kaolin and bentonite clay. Examples of suitable lubricants include, talc, calcium stearate, magnesium stearate, solid polyethylene glycols, sodium lauryl sulfate. In the case of capsules, tablets and pills, the dosage form may also comprise buffering agents.

The tablets may, if desired, be coated using known methods and excipients that may include enteric coating using for example hydroxypropylmethyl cellulose phthalate. The tablets may be formulated in a manner known to those skilled in the art so as to give a sustained release of the NEMO-derived polypeptides of the present invention. Such tablets may, if desired, be provided with enteric coatings by known methods, for example by the use of cellulose acetate phthalate. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Similarly, capsules, for example hard or soft gelatin capsules, containing the active peptide with or without added excipients, may be prepared by known methods and, if desired, provided with enteric coatings in a known manner. The contents of the capsule may be formulated using known methods so as to give sustained release of the active NEMO-derived polypeptides. In such solid dosage forms the active NEMO-derived polypeptides may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Solid compositions of a similar type may also be employed as fillers in soft and hard-filled gelatin capsules using such excipients as lactose or milk sugar as well as high molecular weight polyethylene glycols and the like.

If desired, the NEMO-derived polypeptides of the present invention can be incorporated into slow release or targeted delivery systems such as polymer matrices, liposomes and microspheres. They may be sterilized, for example, by filtration through a bacteria-retaining filter, or by incorporating sterilizing agents in the form of sterile solid compositions that can dissolve in sterile water, or some other sterile injectable medium immediately before use.

The NEMO-derived polypeptides may be formulated into granules with or without additional excipients. The granules may be ingested directly by the patient or they may be added to a suitable liquid carrier (for example, water) before ingestion. The granules may contain disintegrates, e.g. an effervescent couple formed from an acid and a carbonate or bicarbonate salt to facilitate dispersion in the liquid medium.

Dosage forms for topical or transdermal administration of the peptide of this invention include ointments, pastes, creams, lotions, gels, powders, solutions, sprays, inhalants or patches. Transdermal patches have the added advantage of providing controlled delivery of a peptide to the body. The rate can be controlled by either providing a rate controlling membrane or by dispersing the peptide in a polymer matrix or gel. The active component is admixed under sterile conditions with a pharmaceutically acceptable carrier and any needed preservatives or buffers as may be required. Dissolving or dispensing the peptide in the proper medium can make such dosage forms. Absorption enhancers can also be used to increase the flux of the peptide across the skin. Ophthalmic formulation, eardrops, eye ointments, powders and solutions are also contemplated as being within the scope of this invention.

Dosage forms for topical administration may comprise a matrix in which the pharmacologically NEMO-derived polypeptides of the present invention are dispersed so that the peptides are held in contact with the skin in order to administer the peptides transdermally. A suitable transdermal composition may be prepared by mixing the pharmaceutically active NEMO-derived polypeptides with a topical vehicle, such as animal and vegetable fats, oils, petrolatum, waxes, paraffins, starch, tragacanth, cellulose derivatives, polyethylene glycols, silicones, bentonites, silicic acid, talc and zinc oxide, or mixtures thereof, together with a potential transdermal accelerant such as dimethyl sulphoxide or propylene glycol. Alternatively the active NEMO-derived polypeptides may be dispersed in a pharmaceutically acceptable paste, cream, gel or ointment base. The amount of active NEMO-derived polypeptides contained in a topical formulation should be such that a therapeutically effective amount of the peptides are delivered during the period of time for which the topical formulation is intended to be on the skin.

Powders and sprays can contain, in addition to the NEMO-derived polypeptides of this invention, excipients such as lactose, talc, silicic acid, aluminum hydroxide, calcium silicates and polyamide powder, or mixtures of these substances. Sprays can additionally contain customary propellants such as chlorofluorohydrocarbons. The therapeutically active NEMO-derived polypeptides may be formulated into a composition, which is dispersed as an aerosol into the patient's oral or nasal cavity. Such aerosols may be administered from a pump pack or from a pressurized pack containing a volatile propellant.

The therapeutically active NEMO-derived polypeptides used in the method of the present invention may also be administered by continuous infusion either from an external source, for example by intravenous infusion or from a source of the NEMO-derived polypeptides placed within the body. Internal sources include implanted reservoirs containing the NEMO-derived polypeptides to be infused which is continuously released for example by osmosis and implants which may be (a) liquid such as an oily suspension of the peptides to be infused for example in the form of a very sparingly water-soluble derivative such as a dodecanoate salt or a lipophilic ester or (b) solid in the form of an implanted support, for example of a synthetic resin or waxy material, for the NEMO-derived polypeptides to be infused. The support may be a single body containing the entire quantity of the peptides or a series of several bodies each containing part of the quantity of the peptides to be delivered. The amount of active peptides present in an internal source should be such that a therapeutically effective amount of the peptides are delivered over a long period of time.

The invention also relates to the use of an effective amount of a composition comprising a polypeptide fusion construct according to the invention and one or more pharmaceutically acceptable carriers or excipients, for the preparation of a medicament for modulating or treating a disorder regulated by the NF-κB signaling pathway in a subject in need thereof.

According to an advantageous embodiment of said use, said disorder regulated by the NF-κB signaling pathway is selected from the group consisting of inflammatory responses, oncogenesis, and viral infection.

The invention also relates to the use of an effective amount of a composition comprising a polypeptide fusion construct according to the invention and one or more pharmaceutically acceptable carriers or excipients, for the preparation of a medicament for regulating cell proliferation or apoptosis in a subject in need thereof.

The invention also relates to the use of an effective amount of a composition comprising a polypeptide fusion construct according to the invention one or more pharmaceutically acceptable carriers or excipients, for the preparation of a medicament for regulating B or T lymphocytes in antigenic stimulation in a subject in need thereof.

According to an advantageous embodiment of said uses, said subject in need thereof is a human.

According to another advantageous embodiment of said uses, said effective amount ranges from 0.1 mg/Kg/day to 30 mg/Kg/day.

According to another advantageous embodiment of said uses, said composition is administered in a form selected from the group consisting of oral, rectal, nasal, parenteral, intracisternal, intravaginal, intraperitoneal, sublingual, topical, and bucal administration.

According to another advantageous embodiment of said uses, said composition is administered preferably intravenously.

The present invention further provides a method of identifying polypeptides that modulate oligomerization of NEMO by:
a) identifying a candidate polypeptide sequence;
b) creating a polypeptide fusion construct by linking said candidate polypeptide sequence to a polypeptide having a high transduction potential via a spacer sequence;
c) contacting a cell culture with the polypeptide fusion construct; and
d) monitoring the activity of the NF-κB signaling pathway;
e) comparing the activity of the NF-κB signaling pathway in the presence of said polypeptide fusion construct to the activity of the NF-κB signaling pathway in the absence of said polypeptide fusion construct to determine the relative inhibition by said polypeptide fusion construct; and
f) correlating relative inhibition by said polypeptide fusion construct to NEMO oligomerization.

In this method, the candidate polypeptide sequence preferably has a coiled-coil or helical structure. More preferably, the candidate polypeptide sequence has 20-60 amino acids. It is also preferred that the candidate polypeptide sequence be derived from NEMO.

As stated in the embodiments above, the spacer sequence may have a length ranging from 1-35 amino acids, but shorter lengths may also be employed (supra). Examples of the spacer sequence includes: SEQ ID NO: 9 and SEQ ID NO: 10. Additionally, an example of the polypeptide having a high transduction potential is a polypeptide having the amino acid sequence of SEQ ID NO: 1.

In a preferred embodiment, the cell culture contains pre-B 70Z/3 lymphocytes that have been transfected with NF-κB dependent β-galactosidase reporter gene.

In order to ensure that the polypeptide fusion construct is actually incorporated into the cells contained in the cell culture it is desired that the polypeptide fusion construct have an N-terminal cysteine residue. In this manner, the polypeptide fusion construction may be labeled by chemically reacting the cysteine residue with a fluorophore (e.g., BODIPY) thus enabling monitoring of cellular uptake by a technique such as FACS.

Accordingly, the method of identifying polypeptides that modulate oligomerization of NEMO may also include the following steps:
b-1) labeling said polypeptide fusion construct; and
c-1) monitoring cellular uptake of the labeled polypeptide fusion construct.

Further, one of skill in the art may also be able to correlate NF-κB pathway inhibition with modulation of NEMO oligomerization by a pull down experiment with tagged peptides to show that NEMO associates in vivo with the peptides. The oligomeric state of this peptide associated NEMO protein could be characterized (cross-inking, gel filtration). In vitro, Inhibition of the anisotropy increase resulting from the association of fluorescent antennapedia labelled CC2 or LZ peptides with CC2 or LZ peptides, mimicking NEMO oligomerization, could be used to test compounds inhibiting NF-κB pathway in vivo.

Having generally described this invention, a further understanding can be obtained by reference to certain specific examples, which are provided herein for purposes of illustration only, and are not intended to be limiting unless otherwise specified.

EXAMPLES

Materials and Methods

Cell Culture, Stable Transfections and Cell Lines

The grow conditions of the murine pre-B 70Z/3 were as described in Courtois et al., 1997 Mol. cell. Biol. 70Z3-C3 stable cell lines were prepared by electroporation as described in Courtois et al. with the plasmid cx12lacZ-kB (a kind gift from G. R. Crabtree), bearing three tandem copies of NF-κB sites in the IL-2 promoter (Fiering et al., 1990), The human retinoblastoma cell lines Y79 were purchased from the American Type Culture Collection (Manassas, Va.) and grown in RPMI 1640 medium supplemented with 100 U/ml penicillin, 100 μg/ml streptomycin, and 10% fetal calf serum (FCS).

FACS Analysis $0.5 \times 10^6$ 70Z/3-C3 cells in 0.5 ml were incubated at 37° C. for different times and with various concentrations of peptides as indicated in the Figure legends. The cell suspension was centrifugated at 1,000×g at room temperature and the cell pellet was then washed three times with PBS buffer (1 ml), and finally was resuspended with 500 μl of PBS buffer containing 0.1% sodium azide. Fluorescence analysis was performed with a FACSCalibur (BD Biosciences) and a minimum of 15,000 events per sample was selected. All experiments were performed in duplicates.

Peptide Synthesis and Purification

Peptides were synthesized as described in Mousson et al. 2002 (Biochemistry, 41 p13611-p13616), by using continuous-flow Fmoc/tBu chemistry (Chan, W C, and White, P. D. (2000); Fmoc Solid Phase Peptide Synthesis. A practical approach) on an Applied Biosystems (Foster City, Calif.) Pioneer peptide synthesiser. All chemical reagents were purchased from Applied Biosystems. All peptides were blocked at the N-terminus with an acetyl group and at the C-terminus with an amide. A single extra-cysteine residue was incorporated at the N-terminus of the peptides for subsequent specific labeling (see Table 1).

TABLE 1

Sequence of NEMO derived peptides

| Name | Sequence[1] | Theoretical mass (Da) | Experimental mass (Da) | Constructions with NEMO Human sequences |
|---|---|---|---|---|
| BODIPY-Ant | B-CRQIKIWFQNRRMKWKK (SEQ ID NO: 1) | 2805.19 | 2805.06 ± 0.52 | |
| BODIPY-Ant-CC2 (WT) | B-CRQIKIWFQNRRMKWKKSKGMQLEDLRQQLQQAEEALVAKQELIDKLKEEAEQHKIV (SEQ ID NO: 2) | 7433.01 | 7433.33 ± 0.46 | B-CRQIKIWFQNRRMKWKKSKGMQLEDLKQQLQQAEELVAKQEVIDKLKEEAEQHKIV (SEQ ID NO: 13) |
| CC2 (WT) | SKGMQLEDLRQQLQQAEEALVAKQELIDKLKEEAEQHKIV (SEQ ID NO: 3) | 4155.75 | 4155.86 ± 0.53 | SKGMQLEDLKQQLQQAEEALVAKQEVIDKLKEEAEQHKIV (SEQ ID NO: 14) |
| BOPIDY-Ant-CC2 (Mu) | B-CRQIKIWFQNRRMKWKKSKGMQLEDLRQQGQQAEEAGVAKQELGDKLKEEAEQHKIV (SEQ ID NO: 4) | 7265.18 | 7265.04 ± 0.35 | |
| CC2 (Mu) | SKGMQLEDLRQQGQQAEEAGVAKQELGDKLKEEAEQHKIV (SEQ ID NO: 5) | 3987.43 | 3987.43 ± 0.55 | |
| BODIPY-Ant-LZ (WT) | B-CRQIKIWFQNRRMKWKKLKAQADIYKADFQAERHAREKLVEKKEYLQEQLEQLQREFNKL (SEQ ID NO: 6) | 8064.2 | 8063.9 ± 0.48 | B-CRQIKIWFQNRRMKWKKLKAQADIYKADFQAEQAREKLAEKKELLQEQLEQLQREYSKL (SEQ ID NO: 15) |
| LZ (WT) | LKAQADIYKADFQAERHAREKLVEKKEYLQEQLEQLQREFNKL (SEQ ID NO: 7) | 5318.08 | 5318.21 ± 0.5 | LKAQAKIYKADFQAERQAREKLAEKKELLQEQLEQLQREYSKL (SEQ ID NO: 16) |
| BODIPY-Ant-LZ (Mu) | B-CRQIKIWFQNRRMKWKKLKAQADIYKADFQAERHAREKLVEKKEYSQEQLEQSQREFNKL (SEQ ID NO: 8) | 8012.04 | 8011.98 ± 0.26 | |
| LZ (Mu) | LKAQADIYKADFQAERHAREKLVEKKEYSQEQLEQSQREFNKL (SEQ ID NO: 9) | 5265.92 | 5268.82 ± 0.18 | |
| BODIPY-Ant-GCN4 (WT) | B-CRQIKIWFQNRRMKWKKSKGMQRMKQLEDKVEELLSKNYHLENEVARLKKLVGER | 7315.48 | 7314.76 ± 0.40 | |
| NLM-DR | LKAQADIYKARFQAERHAREK (SEQ ID NO: 30) | 2570.94 | 2570.78 +/- 0.21 | LKAQADIYKARFQAERQAREK (SEQ ID NO: 35) |
| BODIPY-Ant-NLM-DR | B-CRQIKIWFQNRRMKWKKLAQADIYKARFQAERHAREK (SEQ ID NO: 31) | 5317.08 | 5316.38 +/- 0.26 | B-CRQIKIWFQNRRMKWKKLAQADIYKARFQAERQAREK (SEQ ID NO: 36) |
| BODIPY-TAT-NLM-DR | B-CYGRKKRRQRRRLKAQADIYKARFQAERHAREK (SEQ ID NO: 32) | 4630.17 | 4630.11 +/- 0.22 | B-CYGRKKRRQRRRLKAQADIYKARFQAERQAREK (SEQ ID NO: 37) |
| BODIPY-R7-NLM-DR | B-CRRRRRRRLKAQAKIYKARFQAERHAREK (SEQ ID NO: 33) | 4181.65 | 4181.60 +/- 0.69 | B-CRRRRRRRLKAQADIYKARFQAERQAREK (SEQ ID NO: 38) |

TABLE 1-continued

Sequence of NEMO derived peptides

| Name | Sequence[1] | Theoretical mass (Da) | Experimental mass (Da) | Constructions with NEMO Human sequences |
|---|---|---|---|---|
| BODIPY-R9-NLM-DR | B-CRRRRRRRLKAQAKIY KARFQAERHAREK (SEQ ID NO: 34) | 4494.02 | 4493.81 +/− 0.23 | B-CRRRRRRRRLKAQADIYKAR RFAQERQAREK (SEQ ID NO: 39) |

(1) In all peptides the N-terminus contains a cysteine residue for convenience of specific peptide coupling with the maleimide group as described in the "Material and Methods".
The sequences of antennapedia, TAT and poly-arginine (R7 or R9) fused to the NEMO sequence (plain text) are highlighted in bold characters.
Residues that may be involved in coiled-coil sequence are underlined and those that were replaced in the CC2 and LZ mutants and in NLM-DR are underlined in bold characters.
B = Bodipy (The C-terminal Bodipy modification has been omitted from the sequences appearing in the Sequence Listing) Within the scope of the present invention it is contemplated that Bodipy and/or the N-terminal cysteine may be removed and used as described herein.

Crude peptides were directly purified by reverse-phase medium-pressure liquid chromatography (MPLC) on a Nucleoprep 20 μM C18 100 Å preparative column, using a linear gradient of acetonitrile (1%/min) in 0.08% aqueous trifluoroacetic acid (TFA) (pH 2) for 60 min at a flow rate of 18 ml/min. The purity of the peptides was verified on a nucleosil 5 μM C18 300 Å analytical column, using a linear gradient of acetonitrile (0.5%/min) in 0.08% aqueous TFA (pH2) for 20 min at a 1 ml/min flow rate. Conjugation of the fluorophore Bodipy® FL N-(2 amino-ethyl)maleimide (Molecular Probes) to the sulfhydryl group was under equimolar conditions at pH 6 in 50 mM ammonium acetate buffer for 30 min in the dark. The mixture was then loaded on a Nucleoprep 20 μM C18 100 Å preparative column to purify the BODIPY conjugated peptide. In cell death experiments, all peptides devoid of BODIPY-labeling were subjected to treatment with iodoacetamide to prevent any oxidation of cysteine residue. All purified peptides were then quantified by amino acid analysis and finally characterized by using positive ion electrospray ionization mass spectrometry (ES+). Once integrity of the peptides and coupling efficiency were verified by mass spectrometry, the extinction coefficients of the peptides were measured at 505 nm or at 280 nm when peptides contained aromatic residues (see Table 1). Stability of the labeling was monitored periodically by measuring the absorbance of peptides at 280 nm and at 505 nm and by calculating the absorbance ratio. All peptides were dissolved in water to stocks of 2 mM.

NF-κB Inhibition Assays

In a first procedure $2.2 \times 10^5$ 70Z/3-C3 cells in 220 μl of RPMI 1640 supplemented with 10% fetal calf serum (FCS) and 50 μM β-mercaptoethanol were placed in a 96-well plate and incubated with various concentrations of peptide (0 to 20 μM) at 37° C. in 5% $CO_2$ incubator. After two hours an equal portion (100 μl) of each cell sample transferred in two wells containing each $10^5$ cells. One aliquot of cells was then treated for 5 hours with lipopolysaccharides from *Salmonella abortus* (Sigma) at 0.5 μg/ml final concentration, and the other one left-treated. After 5 hours, cells were centrifuged at 400×g for 5 min at room temperature and the cell pellets were washed three times with cold PBS (250 μl) by centrifugation. Cells were then lysed in the lysis buffer (25 mM tris-phosphate buffer at pH 7.8 containing 8 mM magnesium chloride, 1 mM dithioerythreitol, 1% Triton X-100, 15% glycerol and a protease inhibitor mixture (Roche)), and samples were centrifuged at 4° C. for 20 min to clarify the lysate. The supernatant was then kept on ice, and 30 μl was then assayed to measure the β-galactosidase activity with a plate luminometer (Berthold) using the galacton-star as chemiluminescent substrate (BD Biosciences Clontech, Bronstein et al., 1989). Background of reaction was measured by mixing for 1 hour 30 μl of lysis buffer with the reaction buffer (196 μl) and the galacton-star substrate (4 μl) provided by BD Biosciences. In a second procedure and a more stringent assay, 70Z/3-C3 cells ($2.2 \times 10^5$ in 220 μl medium) were centrifuged at 400×g at room temperature after peptide internalization for 2 hours, and cell pellets were washed three times with 200 μl of PBS by centrifugation. Cells were then diluted three times with complete medium, and allowed to grow for at least 24 hours. The following steps are identical to the first procedure.

Cell Death Assays

The detection of cell death was performed using the MTS assay provided by Promega (CellTiter 96® $AQ_{ueous}$ one solution cell proliferation assay). Briefly, $0.3 \times 10^6$ Y79 cells in 450 μl were treated with 50 μl of the wild type Ant-CC2 and Ant-LZ peptides (0.1 to 20 μM) or their mutants Ant-CC2 (Mu), Ant-LZ (Mu) or the Ant or left untreated in serum-free RPMI medium at 37° C. After an incubation of 1 or 14 hours, an aliquot of the cell suspension (200 μl, $0.12 \times 10^6$ cells), was then transferee in 96-well plates and mixed with the MTS solution (40 μl) containing the MTS compound and the phenazine ethosulfate. Two hours after, the quantity of formazan produced by viable cells was measured using an automated microplate reader (Bio-TeK Instruments, INC) at 490 nm absorbance. Cell survival was observed under microscope and was estimated as a percentage of the value of untreated controls. The background of the reaction was determined by mixing the MTS solution with cell-free RPMI medium. To increase the sensitivity of the cell death assay, the present inventors used peptides devoid of BODIPY-labeling because the absorption spectra of the fluorophor overlaps with that of the formazan product. All experiments were repeated twice and each experiment condition was repeated in duplicate wells in each experiment.

Analytical Gel Filtration Experiments

The oligomeric states of peptides were determined by filtration as described in Traincard et al., 2003. In brief, 500 μl samples were loaded on a Superdex 75 HR 10/30 column equilibrated in 50 mM Tris-HCl pH 8.0 containing 200 mM NaCl and 0.1 mM DDM, at a constant flow rate of 0.4 ml/min.

The presence of the DDM detergent was added in the equilibrium buffer to minimize the adsorption in the column and to increase the peptide recovery. The column was calibrated in the same equilibrium buffer with blue dextran 2000 (void volume), dithioerythritol (total volume), bovine serum albumin (67 kDa, Rs=35.2 Å), ovalbumine (43 kDa, Rs=27.5 Å), chymotrypsinogen A (25 kDa, Rs=21.1 Å), ribonuclease A (13.7 kDa, Rs=16.4 Å), cytochrome C (12.4 kDa, Rs=17.7 Å) and aprotinin (6.5 KDa, Rs=13.5 Å).

Fluorescence Anisotropy Measurements

Anisotropy measurements were performed with a PTI Quantamaster fluorometer equipped with polarizers for the excitation and emission beams. This instrument uses a PMT in the L-configuration. All experiments were carried out in a 1 cm path-length cuvette at 22° C. with excitation and emission wavelengths at 495 nm and 520 nm, respectively. The bandpass of excitation and emission monochromators was set at 2 and 4 nm, respectively. Steady-state fluorescence anisotropy was expressed as millianisotropy (mA) and was calculated according to the equations: (1) $A=(I_{VV}-GI_{VH})/(I_{VV}+2GI_{VH})$; (2) $G=I_{HV}/I_{HH}$; where A is anisotropy, G is a correction factor for wavelength-dependent distortion and I is the fluorescence intensity component (subscript referring to the vertical and horizontal positioning at the excitation and emission polarizers, respectively). Experiments were at least performed twice and each data is the result of 20 records along a 2 min period. All measurements were carried out in 50 mM Tris-HCl buffer at pH 8 containing 150 mM KCl. The present inventors verified that at the BODIPY-Ant-CC2 and BODIPY-Ant LZ concentration used (1 µM and 0.1 µM respectively), the filter effect was negligible. The BODIPY-Ant-CC2 peptide was preincubated overnight at 22° C. alone or with increasing concentrations (1-125 µM) of CC2 prior to anisotropy measurement. The BODIPY-Ant-LZ peptide (100 nM) was preincubated overnight at 22° C. alone or with 10 µM and 100 µM concentrations of CC2 (see legend FIG. 7) prior to anisotropy measurement. The dissociation constant parameter was estimated by globally fitting the anisotropy data to binding isotherm equation as described in Agou et al. (2004, J Biol Chem.) using Kaleidagraph nonlinear regression software (Synergy Software, reading PA). The binding stoichiometry, n, was estimated from the intersection of lines (dashed lines in FIG. 7) drawn through the descending and plateau region of the anisotropy data.

Results

Rational Design of NEMO Derived Peptides that Block NF-κB Activation

The present inventors previously demonstrated that the minimally trimerization domain of NEMO comprised of the sequence 251 to 337 (FIG. 1A). This region likely contains two coiled-coil sequences of about 35 residues denoted CC2 (residue 253-285) and LZ (301-337) at the N- and C-terminus respectively. Although the structure of the minimal oligomerization domain has not yet been determined, several biochemical studies combined with the fluorescence polarization method prompted us to propose that the CC2/LZ trimer probably forms a six-stranded helical bundle composed of closely packed CC2 and LZ coiled-coils in an antiparallel orientation (Traincard, 2003, submitted). Furthermore PSI-BLAST searches reveal that this domain of NEMO contains a conserved motif of 20 residues called "NEMO like Motif" (NLM) which is shared with four other proteins including ABIN-1 (Heyninck, 1999, J. Cell. Biol.), ABIN-2/NAF (Van Huffel, 2001, J. Biol. Chem), ABIN-3/LIND (Staege, 2001, Immunogenetics) and NRP/optineurin (Schwamborn, 2000, J. Biol. Chem) (FIG. 1B). Interestingly, most of these proteins including the conserved motif of ABIN-1 (Heyninck, 2003, FEBS Letters), the C-terminal domain of NEMO (Le Page, 2001, Virology) and ABIN-2 (Liu WK, 2003, Biochemical Journal) or ABIN-3/LIND (Heyninck, 2003, FEBS letters) proteins have been shown to inhibit NF-κB activation in a dominant-negative manner when overexpressed in cells. Two additional references that disclose ABIN peptides interacting with NF-κB also warrant mention: WO 99/57133 and WO 03/00280.

Since disrupting NEMO oligomerization represents a potential therapeutic strategy for inhibiting NF-κB activation, the present inventors designed NEMO-derived partner peptides that mimic either the CC2 or the LZ sequence (Table 1). It is interesting to note that, unlike the CC2 peptide, the LZ peptide also includes the NLM motif at the N-terminal extremity. To mediate all peptide uptake into cells, the present inventors conjugated a functional analogue at the peptide N-terminus comprised of the 16-amino acid sequence derived from the third helix of the Antennapedia/penetratin protein (Ant). This amphipatic helix acts as an internalization vector (Prochiantz, 2000, Curr. Opin. Cell Biol.). Most of antennapedia fusion peptides were labeled with the BODIPY fluorophore to analyze the transduction potential of each peptide into the cells. Specific labeling was performed by adding a single cystein residue at the extremity of the N-terminus and sequence integrity was verified by mass spectrometry (see "Materials and methods" and Table 1).

Cellular Uptake of NEMO Derived-Peptides Mediated by the Antennapedia Fusion Peptide The uptake of BODIPY labeled NEMO peptides into living cells were monitored by fluorescence activated cell sorting (FACS) which is a conventional tool used to quantify cellular internalization. FIG. 2A shows FACS analyses of cells treated with Ant-CC2 (WT), Ant-CC2 (Mu), Ant-LZ (WT) or Ant-LZ (Mu) BODIPY-peptides for 2 h at 37° C., and were compared with those of the autofluorescence of untreated cells and control cells treated with an equal concentration of free BODIPY or with BODIPY-conjugated BSA. Consistent with the role of antennapedia peptide to transduce peptides and proteins into mammalian cells, 100% of 70Z3-C3-cell line was similarly transduced by the four different NEMO peptides, suggesting that all of the cells in the treated population have a near identical intracellular concentration of NEMO-derived BODIPY-peptides. Comparative analysis indicate that untreated cells and treated cells with BODIPY-BSA or free BODIPY exhibit a similar cell fluorescence, verifying that our extensive washing protocol before FACS analysis was optimal to minimize any contribution of surface-bound peptide in measuring NEMO peptide internalization (see "Materials and methods"). Thus, these data suggest that the observed cellular fluorescence signaling mostly reflects the intracellular concentration of transduced NEMO peptide and not a non-specific adsorption onto the membrane surface.

Then present inventors next investigated the kinetic and concentration dependency of cellular uptake for the Ant-CC2 BODIPY peptide keeping in mind that the transduction of other NEMO peptides should occur in a similar fashion (FIGS. 2B and 2C). FACS analysis 5 h after addition of 70Z3-C3 cell treated with 0.2, 2 or 20 µM BODIPY-Ant-CC2 peptide at 37° C. demonstrate the linear dependency of the intracellular concentration as a function of the incubated concentration of the antennapedia fusion peptide as widely reported in literature (Lindsay, 2002, Current Opinion in Pharmacology). Notably, the cells treated with the Ant-CC2 at 20 µM and at 37° C. already reach maximum intracellular concentration in 30 min and remain unchanged for up to 5 h. Since the time to induce a strong NF-κB activation in response to LPS requires 3-5 hours of cell treatment, these results indicate that the intracellular concentration of each peptide remains constant during the LPS stimulation.

Specific Inhibition of LPS-Induced NF-κB Activation by Cell Permeable CC2 and LZ To analyze the inhibition potential of LPS-induced NF-κB activation by cell permeable BODIPY-Ant-CC2 and BODIPY-Ant-LZ peptides, the present inventors stably transfected the murine pre-B 70Z3 cell line with p12XlacZ-kB, which bears the β-galactosidase reporter gene under the control of the NF-κB transcription factor. When the resulting cell line 70Z3-C3 was treated for 5 hours with LPS (3 μg/ml) a 100 fold-activation of the LacZ gene was observed, indicating that our cellular assay monitors NF-κB activation in response to LPS with extreme sensitivity (FIG. 3A, control "no peptide). Interestingly the incubation of cells with 20 μM of both NEMO-derived polypeptides decreased significantly the NF-κB activation. This lowering was stronger in the presence of BODIPY-Ant-LZ as compared to BODIPY-Ant-CC2. The inhibition effect was essentially due to the NEMO sequence because the presence of the isolated and/or purified antennapedia peptide containing or not containing a N-terminal BODIPY label (BODIPY-Ant or Ant) induces the same level of NF-κB activation as the control (FIG. 3A). Note that the basal NF-κB activity measured in the absence of LPS was very similar in all samples indicating that both CC2 and LZ peptides abolish the responsiveness to LPS without affecting the intrinsic basal NF-κB activity. This was essential to minimize the in vivo cytotoxicity, resulting mainly from apoptosis induced by inhibition of NF-κB (Chen, 2003, Nature Med.).

To determine whether the BODIPY-Ant-LZ or the BODIPY-Ant-CC2 peptide is the most efficient inhibitor, the present inventors next measured the concentration dependent inhibition of each peptide. As shown in FIG. 3B, both NEMO peptides exhibit NF-κB dose dependant inhibition of NF-κB in response to LPS. BODIPY-Ant-LZ inhibited NF-κB to a greater extent than BODIPY-Ant-CC2 did with $IC_{50}$ values of 3 μM and 22 μM respectively (FIG. 3C). This striking difference could be explained by the NLM motif included in the LZ sequence. Consistent with the intracellular nature of the NEMO target, both LZ and CC2 peptides not fused to the antennapedia protein transduction domain (PTD) exhibited the same level of activation as the control (FIG. 3 D), confirming that NEMO derived peptides must cross the cell membrane for inhibition of NF-κB. Taken together these results indicate that peptides that mimic the two coiled-coil sequences of the NEMO oligomerization domain are potent peptide inhibitors of NF-κB activation in response to LPS.

Mutations in the Hydrophobic Core of the LZ and CC2 Coiled-Coils Disrupt their Specific Inhibition of the NF-κB Signaling Pathway Theoretically, if BODIPY-Ant-LZ or BODIPY-Ant-CC2 peptide inhibit NF-κB activation through specific binding to the NEMO oligomerization domain, mutations that disrupt the coiled-coil association should therefore exhibit impaired abilities to inhibit NF-κB inhibition. α-helical coiled-coil interactions have been extensively studied and most of the rules governing their specific assembly have been well documented (Vinson, 2002, Mol. Cell. Biol.). The coiled-coil interface that is represented by the first (a) and fourth position (d) of the heptad repeat is generally occupied by hydrophobic amino acids. Proline or glycine is largely excluded to preserve the helical architecture. Core polar residues are destabilizing relative to leucine substitutions, especially when changes occur at d positions. Considering these rules, the present inventors synthesized a variant of BODIPY-Ant-LZ containing two mutations L→S at the d positions (BODIPY-Ant-LZ (Mu) and a variant of BODIPY-Ant-CC2 containing two mutations L→G and one mutation I→G at the a positions (BODIPY-Ant-CC2 (Mu) (FIGS. 4A and 4B, and Table 1). To test the effects of these mutations on the potential inhibition of NF-κB activation, the present inventors developed a more stringent cellular assay that consists of the internalization of the peptides for 2 hours followed by an extensive washing of 70Z3-C3 cells to remove any remaining peptide in the extracellular media. Cells were allowed to grow for at least 24 hours before LPS-induced NF-κB activation. In this way, peptide interference with the receptor binding LPS was excluded. As with the cellular assay described above, the BODIPY-Ant-CC2 (WT) and the BODIDY-Ant-LZ (WT) also inhibited NF-κB activation with a 1.7 and 5.8-fold reduction respectively (FIGS. 4A and 4B) when used at a 10 μM concentration. This indicates that the peptides do not competitively act on the receptor binding of LPS. As expected, the presence of the CC2 variant (BODIPY-Ant-CC2 (Mu)) did not affect the NF-κB activation since β-galactosidase activity was equivalent to that of the control (FIG. 4A, no peptide). In response to LPS, NF-κB is more strongly activated in the presence of the BODIPY-Ant LZ mutant than in the presence of wild type. However, unlike the BODIPY-Ant-CC2 (Mu), a slight inhibition of the LZ mutant was observed when compared to the control (15%). When taken together, these data demonstrate that CC2 and LZ mutants are unable to inhibit the LPS-induced NF-κB activation as effectively the wild type did.

Inhibition of NF-κB Activation is Mediated by a Specific Coiled Coil Interaction of the LZ Peptide.

Computational analyzes using the program MULTICOIL (Wolf, 1997, Protein Science) predicted that greater than 5% of all putative ORFs found in sequenced genomes are predicted to contain coiled-coil motifs (Newman, 2000, Proc. Natl. Acad. Sci. USA) and that approximately 2-4% of amino acids in proteins are estimated to adopt coiled-coil folds (Berger, 1995, Proc. Natl. Acad. Sci. USA). This abundance raises the question if the NEMO derived-LZ peptide maintains its coiled-coil interaction partnering specificity in vivo. To address this question, the present inventors synthesized another coiled-coil peptide that mimics the sequence of the GCN4 leucine zipper and tested its ability to inhibit NF-κB activation. BODIPY-Ant-GCN4 contained the antennapedia sequence at its N-terminus and a short SKGMQ linker (SEQ ID NO: 9) identical to the CC2 sequence for convenience of peptide delivery (Table 1). It was also labeled at its N-terminus with BODIPY to monitor its cellular uptake by FACS (data not shown). The GCN4 peptide displays a low sequence similarity with the LZ sequence of NEMO (22%) but identical residues are mostly represented by leucines at d positions (FIG. 5). These residues contribute to most of the energy to coiled-coil oligomerization stability (Vinson, 2002, Mol. Cell. Biol.). Note that a positions which are important for coiled-coil specificity (Vinson, 2002, Mol. Cell. Biol) are composed of a set of different amino acids. While GCN4 is composed of hydrophobic residues and the typical asparagine residue, the LZ of NEMO contains two charged amino acids R and K (FIG. 4B and FIG. 5A). Thus, these residues, which are located at the coiled coil interface likely, contributes to the selectivity of coiled coil interaction.

FIG. 5B shows the effect of the BODIPY-Ant-GCN4 at a 10 μM concentration on the inhibition of NF-κB activation in response to LPS. To compare the effects of coiled coil sequences, the present inventors used the stringent cellular assay described above. BODIPY-Ant-GCN4, unlike BODIPY-Ant-LZ, has no ability to inhibit NF-κB activation since the level of NF-κB activation was near that of the control without peptide. Taken together, these results strongly support the hypothesis that the LZ peptide of NEMO inhibits NF-κB activation through selective coiled-coil interactions.

The Antennapedia Sequence Induces Monomerization of NF-κB Peptidic Inhibitors

The antennapedia sequence is a protein transduction domain (PTD) which adopts an alpha-helical amphiphatic structure (Prochiantz, 2000, Curr. Opin. Cell Biol.). When fused to the N terminus of a coiled-coil sequence like CC2 or LZ, the antennapedia could alter the coiled-coil association by covering the hydrophobic interface of the coiled-coil through intramolecular interactions. To examine the effect of N-fusion of the antennapedia peptide on the oligomerization properties of the CC2 and the LZ peptides, the present inventors analyzed peptides containing or not containing the antennapedia sequence at their N-terminus by gel filtration. As shown in FIG. 6, all peptides containing an N-terminal fusion of antennapedia co-elute with an elution volume corresponding to their monomeric forms as compared to globular protein markers. Note that the present inventors had to add a detergent in the buffer below its cmc to improve peptide recoveries. When injected at the same 10 μM concentration, CC2 wild type and LZ wild type without the antennapedia N-fusion oligomerize. CC2 (WT) forms a trimer whereas LZ (WT) forms a dimer as recently reported (Traincard et al). As expected, when a CC2 mutant was chemically obtained with three of its aliphatic residues at positions replaced with glycine residues, it lost its ability to oligomerize (bottom panel, dashed line). The effect of the two L→S mutations at d positions was less strong with LZ (mutant). However, the present inventors still detected dimerization of the LZ mutant at a 10 μM concentration (dashed line) although its association was markedly reduced by mutations as compared to the wild type LZ (solid line). Taken together, these data indicate that the N-fusion of the antennapedia sequence to both CC2 and LZ peptides alter homotypic coiled-coil interactions, facilitating the monomerization of the NEMO derived-peptides. Furthermore these results also show that residue changes at a and d position alter oligomerization of LZ and CC2 peptides. Thus, it is likely that the synthetic peptides form α-helical coiled-coil structures.

Homo- and Heterotypic Interactions of CC2 and LZ Peptides with and without the N-Fusion of Antennapedia Sequence.

Because the N-fusion of antennapedia modifies the oligomerization properties of the CC2 and LZ peptides, the present inventors next studied by fluorescence polarization whether the Ant-CC2 and the Ant-LZ monomers labeled with BODIPY could bind to the NEMO-derived polypeptides devoid of the antennapedia sequence. These peptides CC2 and LZ may be also considered as the in vivo binding target for both cell permeable BODIPY-Ant-CC2 and BODIPY-Ant-LZ NF-κB inhibitors. FIG. 7 shows a typical binding isotherm for the interaction of various concentrations of the CC2 peptide with a fixed concentration of the BODIPY-Ant-CC2. The shape of the binding curve is not sigmoidal, indicating that CC2 binds to the BODIPY-Ant-CC2 peptide without cooperativity. The stoichiometry calculated from the intercept between the tangent of the initial part of the anisotropy and the asymptote is equal to 0.8. Taking into account this stoichiometry, the dissociation constant $K_D$ is 15.2 μM. Similar results were obtained when a fixed concentration of the BODIPY-Ant-LZ was titrated with various concentrations of the CC2 peptide as the present inventors previously reported (Inset FIG. 7, Traincard et al.). Collectively, these data demonstrate that both Ant-CC2 and Ant-LZ monomers binds in vitro to the CC2 peptide composing the minimal oligomerization domain of NEMO.

Cell Death in Human Retinoblastoma Cell is Induced by NF-κB Inhibitors Ant-CC2 and Ant-LZ, but not by their Mutants Ant-CC2 (Mu) and Ant-LZ (Mu)

It has become clear that constitutively activated NF-κB transcription factors have been associated with several aspects of tumorigenesis (Karin review), including most of six essential alterations in cell physiology that dictate the conversion of normal human cells into cancer cells (Hanahan, 2000, Cell for review). This led to a significant enthusiasm for the use of NF-κB inhibitors as a new anti-cancer therapy. Promising results have been reported recently using proteasome inhibitors or the SN50 peptide that blocks the nuclear translocation (Orlowski, 2002, Trends in Molecular Medicine; Mitsiades, 2002, Blood). However, the specificity of these agents on NF-κB inhibition have been questioned. Poulaki et al. (2002, Am J Pathol.) showed recently that the treatment of the human retinoblastoma (Rb) cell lines Y79 with SN50 peptide induced apoptosis of cancer cells. Sequence alignment of murine and human NEMO proteins indicate that the minimal oligomerization domain of NEMO is strictly conserved, suggesting that similar effects of NF-κB inhibition could be observed in rodent as well as in human cells.

Given that specific NF-κB inhibition may trigger apoptosis of cancer cells, the present inventors examined the effects of both cell-permeable Ant-LZ and Ant-CC2 peptides on human retinoblastoma cell viability. In these experiments, the present inventors used NEMO-derived polypeptides without a N-terminal BODIPY labeling to prevent any interference with the MTS assay (see "Materials and Methods"). As shown in FIG. 7, the present inventors found a dose dependence of the Y79 cell viability when cells were treated for 3 hours with Ant-CC2 (FIG. 8A) or Ant-LZ (FIG. 8B). The effect of the Ant-LZ peptide on cell death was stronger than that of the Ant-CC2. This induction of cell death was significant since Rb cell survival was 20% and 65% with the Ant-LZ and the Ant-CC2 peptides respectively when cancer cells were treated for 3 hours at a 20 μM concentration. Remarkably, the same cell treatment with the Ant-CC2 (Mu) (FIG. 8A) or with the Ant-CC2 (Mu) (FIG. 8B) did not induce concentration cell death as did WT peptides. These effects on cell death were essentially due to the NEMO sequence because a longer treatment of Y79 cell lines with the antennapedia peptide did not affect cell survival (FIG. 8C). In contrast, 80% and 55% of Y79 cell died in the presence of Ant-LZ and Ant-CC2 respectively at 5 μM concentration (FIG. 8C). Taken together, these results indicate that specific NF-κB inhibition by Ant-CC2 and Ant-LZ peptides induce cell death in Rb cell lines, validating the use of specific NF-κB inhibitors as anticancer chemotherapy.

In the absence of the pro-inflammatory signals, all peptides assayed have no detectable cytotoxicity for lymphocytes B tested at a concentration up to 30 μM according to the MTS assay, the direct observation under microscope, and the forward scatter-FSC and side scatter-SSC parameters deduced from FACS analyses. However, the present inventors could detect a slight cell death by FACS in a concentration-dependent manner when LPS stimulated the pre-B lymphocytes in the presence of NEMO-derived polypeptides. The cellular proportion of cell death was 9% in the absence of stimuli at a 20 μM concentration of Ant-CC2 whereas it increased at 13% after LPS stimulation (data not shown). This was in agreement with the role of the NF-κB pathway in protecting cells from apoptosis. The cell death was more pronounced and fast on the Rb cell lines Y79 in which constitutive NF-κB activity has been reported (Poulaki, 2002, Am J Pathol.). The present inventors did not demonstrate here by the Annexin V labeling and the TUNEL method that the NEMO peptides-induced cell death is indeed apoptosis. Nevertheless considering the role of the NF-κB pathway in the regulation of apoptosis, it is likely that the cell death induced by NEMO-derived polypeptides is apoptotic in nature.

The results set forth above, regardless of the nature of the future NF-κB inhibitors (organic or peptidomimetic compounds), targeting NEMO's oligomerization will remain a more attractive and promising strategy as compared to those of IKK kinase activity and of NEMO-kinase association because this molecular event strictly depend on the pro-inflammatory signal. Therefore, such drugs would interfere less with the basal NF-κB activity in normal cells that is required for cell viability.

Peptides Derived from the N-Terminal Region of Wild-Type NEMO

The present inventors explored the N-terminal region of the wild-type NEMO, in particular the NLM conserved motif (residues 293-322 of SEQ ID NO: 12) appearing in FIG. 1A. To this end, the following sequences were produced (see Table 1 for the corresponding sequence):

```
NLM-DR       (SEQ ID NO: 30)

Ant.NLM-DR   (SEQ ID NO: 31)

Tat NLM-DR   (SEQ ID NO: 32)

R7-NLM-DR    (SEQ ID NO: 33)

R9-NLM-DR    (SEQ ID NO: 34)
```

NLM-DR is a 21 amino acid "motif" (and the corresponding wild type NLM covering the same amino acid range) derived from the larger 30 amino acid conserved NLM motif set forth in FIG. 1A. The NLM-DR has been mutated from the wild type NLM sequence in that the aspartic acid at residue 11 in the wild type sequence has been replaced by an arginine (see Table 1 and SEQ ID NO: 30).

The present inventors compared NLM-DR to the corresponding NLM peptide by measuring the respective cooperativity indices, which evidence an advantage of NLM-DR mutated peptide over the wild-type.

The calculation of the "cooperativity indice" by means of Hill coefficient is based on the following formula Boundmax×L$^n$/(KD$^n$+L$^n$)

Wherein

Boundmax is the maximum concentration of the bound ligand,

L is the concentration of the free ligand, n is the cooperativity indice and

KD, is the affinity constant of the ligand by the protein.

The cooperative indices calculated by means of the Hill coefficient calculation are:

For the mutant NLM peptide (NLM-DR)—a dissociation constant Kd of 170 μM and a cooperativity indice of 1.4 (1326 μM); and For the corresponding wild-type NLM peptide (NLM)—a dissociation constant Kd of 240 μM and a cooperativity indice of 2.1 (99642 μM).

If these values were to be compared to those obtained from the curves without accounting for cooperativity, the affinity of NLM-DR peptide would be 75 times higher than the affinity of wild-type NLM peptide.

The present inventors also evaluated the biologically relevant results for the aforementioned forms of NLM-DR as they apply to the inhibition of NF-κB activation pathway, IC50 and toxicity results (FACS). The results are presented in Table 2:

TABLE 2

Properties of NLM-DR derived peptides

| Peptide | Cytotoxicity* | | | Cellular uptake relative efficiency (FACS) | IC 50 |
|---|---|---|---|---|---|
| | MTS Assay | Cell morphology | | | |
| | | FACS | Microscope | | |
| BODIPY-Ant-NLM-DR | no | + | + | + | 1.1 μM |
| BODIPY-TAT-NLM-DR | no | no | no | + | 1 μM |
| BODIPY-R9-NLM-DR | no | no | no | ++ | 0.9 μM |
| BODIPY-R7-NLM-DR | n.d. | no | no | ++++ | 0.9 μM |

*Cytotoxicity analysed by the indicated technique is scaled from no toxicity (no) to high toxicity (++++); the MTS cell proliferation assay was from Promega;
n.d. = not determined.

Numerous modifications and variations on the present invention are possible in light of the above teachings. It is, therefore, to be understood that within the scope of the accompanying claims, the invention may be practiced otherwise than as specifically described herein.

REFERENCES

1. Agou, F., Ye, F., Goffinont, S., Courtois, G., Yamaoka, S., Israël, A. and Véron, M. (2002) NEMO trimerizes through its coiled-coil C-terminal domain. J. Biol. Chem., 20, 17464-17465

2. Agou F., Traincard F., Vinolo E., Courtois G., Yamaoka S., Israël A., Véron M. (2004) The trimerization domain of NEMO is composed of the interacting C-terminal CC2 and LZ coiled-coil subdomains. J Biol Chem. 2004 Jul. 2; 279(27):27861-9

3. Berger B, Wilson D B, Wolf E, Tonchev T, Milla M, Kim P S. (1995) Predicting coiled coils by use of pairwise residue correlations. Proc Natl Acad Sci USA. August 29; 92 (18): 8259-63.

4. Bronstein I, Edwards B, Voyta J C. 1,2-dioxetanes: novel chemiluminescent enzyme substrates. Applications to immunoassays. J Biolumin Chemilumin. 1989 July; 4(1): 99-111.

5. Carter R S, Geyer B C, Xie M, Acevedo-Suarez C A, Ballard D W. (2001) Persistent activation of NF-kappa B by the tax transforming protein involves chronic phosphorylation of IkappaB kinase subunits IKKbeta and IKKgamma. J Biol Chem. July 6; 276(27):24445-8. Epub 2001 Apr. 26.

6. Chan D C and Kim P S. (1998) HIV entry and its inhibition. Cell. 1998 May 29; 93(5):681-4. Review. No abstract available.

7. Mike Chang, Lianshan Zhang, James P. Tam, and Elaine Sanders-Bush (2000) Dissecting G Protein-coupled Receptor Signaling Pathways with Membrane-permeable Blocking Peptides. J. Biol. Chem., March 2000; 275: 7021-7029.

8. Lee-Wei Chen, Laurence Egan, Zhi-Wei Li, Florian R. Greten, Martin F. Kagnoff, Michael Karin. (2003) The two faces of IKK and NF-kappaB inhibition: prevention of systemic inflammation but increased local injury following intestinal ischemia-reperfusion Nature Medicine 9, 575-581 (May 1, 2003)
9. Colman, P. M. et al. (2003) The structural biology of Type I viral membrane fusion. Nature Rev. Mol. Cell Biol., 4, 309-317
10. Courtois, G., Whiteside, S. T., Sibley, C. H. and Israël, A. (1997) Characterization of a mutant cell line that does not activate NF-κB in response to multiple stimuli. Mol. Cell. Biol., 17, 1441-1449.
11. Döffinger, R., Smahi, A., Bessia, C., Geissman, F., Feinberg, J., Durandy, A., Bodemer, C., Kenwrick, S., Dupuis-Girod, S., Blanche, S., Wood, P., Rabia, S. H., Headon, D. J., Overbeek, P. A., Le Deist, F., Holland, S., Belani, K., Kumararatne, D. S., Fisher, A., Shapiro, R., Conley, M. E., Reimund, E., Kalhoff, H., Abinun, M., Munnich, A., Israël, A., Courtois, G. and Casanova, J.-L. (2001) X-linked anhidrotic ectodermal dysplasia with immunodeficiency is caused by impaired NF-κB signaling. Nature Genet., 27, 277-285.
12. Eckert, D. M., and Kim, P. S. (2001) Mechanisms of viral membrane fusion and its inhibition. Ann. Rev. Biochem., 70, 777-810
13. S Fawell, J Seery, Y Daikh, C Moore, L L Chen, B Pepinsky, and J Barsoum (1994) Tat-Mediated Delivery of Heterologous Proteins into Cells PNAS 1994; 91: 664-668.
14. Fiering S., Northrop J. P., Nolan G. P., Mattila P. S., Crabtree G. R., Herzenberg L. A. (1990) Single cell assay of a transcription factor reveals a threshold in transcription activated by signals. Genes Dev., 4, 1823-34.
15. Ghosh, S., May, M. J. and Kopp, E. B. (1998) NF-κB and Rel proteins: evolutionarily conserved mediators of immune responses. Annu. Rev. Immunol., 16, 225-260.
16. Hanahan D. and Weinberg R. A. (2000) The Hallmarks of Cancer. Cell, 100, 57-70.
17. Heyninck K, De Valck D, Vanden Berghe W, Van Criekinge W, Contreras R, Fiers W, Haegeman G, Beyaert R. (1999) The zinc finger protein A20 inhibits TNF-induced NF-kappaB-dependent gene expression by interfering with an RIP- or TRAF2-mediated transactivation signal and directly binds to a novel NF-kappaB-inhibiting protein ABIN. J Cell Biol. 1999 Jun. 28; 145(7):1471-82.
18. Heyninck, K., Kreike, M. M. and Beyaert, R. (2003) Structure-function analysis of the A20-binding inhibitor of NF-κB activation, ABIN-1. FEBS Lett., 26956, 1-6.
19. Yinling H U, Veronique BAUD, Takefumi O G A, Keun I L KIM, Kazuhiko YOSHIDA and Michael KARIN (2001) IKKγ controls formation of the epidermis independently of NF-κB Nature 410, 710-714
20. Inohara, N., Koseki, T., Lin, J., del Peso, L., Lucas, P. C., Chen, F. F., Ogura, Y. and Nunez, G. (2000) An induced proximity model for NF-κB activation in the Nod1/RICK and RIP signaling pathways. J. Biol. Chem., 275, 27823-27831.
21. Israel, A. (2000) The IKK complex: an integrator of all signals that activate NF-κB?Trends Cell. Biol., 10, 129-133.
22. J. Kevin Judice, Jeffrey Y. K. Tom, Wei Huang, Terri Wrin, Joann Vennari, Christos J. Petropoulos, and Robert S. McDowell (1997) Inhibition of HIV type 1 infectivity by constrained α-helical peptides: Implications for the viral fusion mechanism PNAS 94: 13426-13430.
23. Karin, M. (1999) The beginning of the end: IκB Kinase (IKK) and NF-κB activation. J. Biol. Chem., 274, 27339-27342.
24. Kovalenko, A., Chable-Bessia, C., Cantarella, G., Israël, A., Wallach, D. and Courtois, G. (2003) The tumor suppressor CYLD negatively regulates NF-κB signalling by deubiquitination. Nature, 424, 801-805.
25. Le Page C., Popescu O., Genin P., Lian J., Paquin A., Galipeau J. and Hiscott J. (2001) Disruption of NF-kappa B signaling and chemokine gene activation by retroviral mediated expression of IKK gamma/NEMO mutants. Virology, 286, 422-33.
26. Yao-Zhong Lin, Song Yi Yao, Ruth Ann Veach, Troy R. Torgerson, and Jacek Hawiger (1995) Inhibition of Nuclear Translocation of Transcription Factor NF-κB by a Synthetic Peptide Containing a Cell Membrane-permeable Motif and Nuclear Localization Sequence. J. Biol. Chem., June 1995; 270: 14255-14258.
27. Mark A. Lindsay (2002) Peptide-mediated cell delivery: application in protein target validation, Current Opinion in Pharmacology, Volume 2, Issue 5, 1 October, Pages 587-594
28. Liu W.-K., Yen, P.-F., Chien, C.-Y., Fann, M.-J., Su, J. Y. and Chou, C. K. (2003) ABIN-2 disrupts the interaction of RIP with IKKγ to block NF-κB activation and potentiate apoptosis. Biochemical Journal
29. May, M. J. et al. (2000) Selective inhibition of NF-κB activation by a peptide that blocks the interaction of NEMO with the IκB kinase complex. Science, 289, 1550-1554
30. May, M. J., Marienfield, R. B. and Ghosh, S. (2002) Characterization of the IκB-kinase NEMO binding domain. J. Biol. Chem., 277, 45992-46000
31. Meinkoth J, Wahl G. (1984) Hybridization of nucleic acids immobilized on solid supports. Anal Biochem. May 1; 138(2):267-84
32. Mitsiades N, Mitsiades C S, Poulaki V, Chauhan D, Richardson P G, Hideshima T, Munshi N, Treon S P, Anderson K C. (2002) Biologic sequelae of nuclear factor-kappaB blockade in multiple myeloma: therapeutic applications. Blood. 2002 Jun. 1; 99(11):4079-86.
33. May C. Morris, Julien Depollier, Jean Mery, Frederic Heitz, Gilles Divita (2001) A peptide carrier for the delivery of biologically active proteins into mammalian cells Nature Biotechnology 19, 1173-1176
34. Mousson, F., Coic, Y.-M., Baleux, F., Beswick, V., Sanson, A. and Neumann, J.-M. (2002) Deciphering the role of individual acyl chains in the interaction network between phosphatidylserines and a single-spanning membrane protein. Biochemistry 41, 13611-13616.
35. Newman, J. R. S., Wolf E. and Kim P. S. (2000) From the cover: A computationally directed screen identifying interacting coiled coils from *Saccharomyces cerevisiae*. Proc. Natl. Acad. Sci. U.S.A., 97, 13203-13208.
36. Robert Z. Orlowski and Albert S. Baldwin, Jr. (2002) NF-κB as a therapeutic target in cancer Trends in Molecular Medicine, Volume 8, Issue 8, Aug. 1, 2002, Pages 385-389
37. Pawson, T. and Nash, P. (2003) Assembly of cell regulatory systems through protein interaction domains. Science, 300, 445-452.
38. Joel L. Pomerantz and David Baltimore. (2002) Two Pathways to NF-κB Molecular Cell 2002 10: 693-695
39. Poulaki V., Mitsiades C. S., Joussen A. M., Lappas A., Kirchhof B., Mitsiades N. (2002) Constitutive nuclear factor-kappaB activity is crucial for human retinoblastoma cell viability. Am J Pathol., 161, 2229-2240.

40. Poyet, J.-L., Srinivasula, S. M., Lin, J-H, Fernandes-Alnmeri, T., Yamaoka, S., Tsichlis, P. N. and Alnemri, E. S. (2000) Activation of yhe IκB kinases by RIP via IKKγ/NEMO-mediated oligomerization. J. Biol. Chem., 275, 37966-37977.

41. Poyet, J.-L., Srinivasula, S. M. and Alnemri, E. S. (2001) vClap, a caspase-recruitment domain-containing protein of equine Herpesvirus-2, persistently activates the IκB kinases through oligomerization of IKKγ. J. Biol. Chem., 276, 3183-3187

42. Prochiantz, A. (2000) Messenger proteins, homeoproteins, TAT and others. Curr. Opin. Cell Biol., 12, 400-406.).

43. Sambrook et al., Molecular Cloning: A Laboratory Manual, Cold Spring Harbor Laboratory Press, New York (1989).

44. Santoro, G., Rossi, A. and Amici, C. (2003) NF-κB and virus infection: who controls whom. EMBO J., 22, 2552-2560.

45. Klaus Schwamborn, Robert Weil, Gilles Courtois, Simon T. Whiteside, and Alain Israël (2000) Phorbol Esters and Cytokines Regulate the Expression of the NEMO-related Protein, a Molecule Involved in a NF-κB-independent Pathway J. Biol. Chem., July 2000; 275: 22780-22789.

46. Uwe Senftleben, Yixue Cao, Gutian Xiao, Florian R. Greten, Gertraud Krähn, Giuseppina Bonizzi, Yi Chen, Yinling Hu, Abraham Fong, Shao-Cong Sun, and Michael Karin. (2001) Activation by IKK of a Second, Evolutionary Conserved, NF-κB Signaling Pathway Science August 24; 293: 1495-1499.

47. T. F. Smith and M. S. Waterman. (1981) Comparison of biosequences Adv. Appl. Math., 2:482-489

48. Souroujon M. C. and Mochly-Rosen D. (1998) Peptide modulators of protein-protein interactions in intracellular signaling. Nat Biotechnol., 16, 919-924.

49. Staege, H.; Brauchlin, A.; Schoedon, G.; Schaffner, A. (2001) Two novel genes FIND and LIND differentially expressed in deactivated and Listeria-infected human macrophages. Immunogenetics 53: 105-113

50. Stroh C, Held J, Samraj A K, Schulze-Osthoff K. Specific inhibition of transcription factor NF-kappaB through intracellular protein delivery of IkappaBalpha by the Herpes virus protein VP22 (2003) Oncogene. August 14; 22(34): 5367-73.

51. Eric D. Tang, Naohiro Inohara, Cun-Yu Wang, Gabriel Nuñez, and Kun-Liang Guan. (2003) Roles for homotypic interactions and transautophosphorylation in B kinase (IKK) activation. J Biol. Chem. Vol. 278, 38566-38570

52. Tegethoff, S. et al. (2003) Tetrameric oligomerization of IκB kinase γ is obligatory for IKK complex activity and NF-κB activation Mol. Cell. Biol., 23, 2029-2041

53. Thompson, J. D., Higgins, D. G. and Gibson, T. J. (1994) CLUSTAL W: improving the sensitivity of progressive multiple sequence alignment through sequence weighting, position-specific gap penalties and weight matrix choice. Nucl. Acids. Res., 22, 4673-4680.

54. Trompouki, E., Hatzivassilou, E., Tsichritzis, T., Farmer, H., Ashworth, A. and Mosialos, G. (2003) CYLD is a deubiquitinating enzyme that negatively regulates NF-κB activation by TNFR family members. Nature, 424, 793-796

55. Sofie Van Huffel, Filip Delaei, Karen Heyninck, Dirk De Valck, and Rudi Beyaert. (2001) Identification of a Novel A20-binding Inhibitor of Nuclear Factor-κB Activation Termed ABIN-2 J. Biol. Chem., August 2001; 276: 30216-30223.

56. Vinson, C., Myakishev, M., Acharya, A., Mir, A. A., Moll, J. R. and Bonovich M. (2002) Classification of human B-Zip proteins based on dimerization properties. Mol. Cell. Biol., 22, 6321-6335.

57. Wolf E., Kim, P. S. and Berger, B. (1997) MultiCoil: A program for predicting two- and three-stranded coiled coils. Protein Sci., 6, 1179-1189.

58. Ebrahim Zandi, David M. Rothwarf, Mireille Delhase, Makio Hayakawa, and Michael Karin. (1997) The IκB Kinase Complex (IKK) Contains Two Kinase Subunits, IKKα and IKKβ, Necessary for IκB Phosphorylation and NF-κB Activation Cell 91: 243-252.

59. Zonana, J., Elder, M. E., Schneider, L. C., Orlow, S. J., Moss, C., Golabi, M., Shapira, S. K., Farndon, P. A., Wara, D. W., Emmal, S. A. and Ferguson, B. M. (2000) A novel X-linked disorder of immune deficiency and hypohydrotic ectodermal dysplasia is allelic to incontinentia pigmenti and due to mutations in IKK-γ (NEMO). Am. J. Hum. Genet. 67, 1555-1562.

The invention claimed is:

1. A polypeptide fusion construct that inhibits signalling via NF-κB comprising:
   a polypeptide having a high transduction potential, and
   an amino acid sequence selected from the group consisting of SEQ ID NO: 3, SEQ ID NO: 7, SEQ ID NO: 14, SEQ ID NO: 16, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, and SEQ ID NO: 39, or a variant thereof having one amino acid substitution;
   wherein said polypeptide having a high transduction potential and said amino acid sequence are optionally linked by an amino acid spacer sequence.

2. The polypeptide fusion construct of claim 1, wherein said polypeptide fusion construct disrupts NEMO (NF-κB essential modulator) oligomerization.

3. The polypeptide fusion construct of claim 1, which is linked by an amino acid spacer sequence having a length ranging from 1-35 amino acids.

4. The polypeptide fusion construct of claim 3, wherein said amino acid spacer sequence is selected from the group consisting of SEQ ID NO: 9 and SEQ ID NO: 10.

5. The polypeptide fusion construct of claim 1, wherein said polypeptide having a high transduction potential comprises the amino acid sequence of SEQ ID NO: 1.

6. The polypeptide fusion construct of claim 5, wherein the polypeptide fusion construct has the amino acid sequence selected in the group consisting of SEQ ID NO: 2, SEQ ID NO: 6, SEQ ID NO: 13 and SEQ ID NO: 15.

7. A method of inhibiting the NF-κB signaling comprising contacting in vitro an eukaryotic cell with the polypeptide fusion construct of claim 1.

8. A method of disrupting NEMO oligomerization comprising contacting in vitro NEMO with the polypeptide fusion construct of claim 1.

9. A method of treating a disorder regulated by NF-κB signaling comprising:
   administering an effective amount of a composition comprising a polypeptide fusion construct of claim 1 and one or more pharmaceutically acceptable carriers or excipients, to a subject in need thereof.

10. The method of claim 9, wherein said subject in need thereof is a human.

11. The method of claim 9, comprising administering an effective amount of the polypeptide fusion construct ranging from 0.1 mg/Kg/day to 30 mg/Kg/day.

12. The method of claim 9, wherein said disorder regulated by NF-κB signaling is selected from the group consisting of inflammatory responses, oncogenesis, and viral infection.

13. The method of claim 9, comprising administering said composition in a form selected from the group consisting of oral, rectal, nasal, parenteral, intracisternal, intravaginal, intraperitoneal, sublingual, topical, and bucal administration.

14. The method of claim 9, comprising administering said composition intravenously.

15. A method for regulating cell proliferation or apoptosis comprising administering to a subject in need thereof an effective amount of a composition comprising the polypeptide fusion construct of claim 1 and one or more pharmaceutically acceptable carriers or excipients.

16. The method of claim 15, wherein said subject in need thereof is a human.

17. The method of claim 15, comprising administering an effective amount of the polypeptide fusion construct ranging from 0.1 mg/Kg/day to 30 mg/Kg/day.

18. The method of claim 15, comprising administering said composition in a form selected from the group consisting of oral, rectal, nasal, parenteral, intracisternal, intravaginal, intraperitoneal, sublingual, topical, and bucal administration.

19. The method of claim 15, comprising administering said composition intravenously.

20. A method for regulating B or T lymphocytes in antigenic stimulation comprising administering to a subject in need thereof an effective amount of a composition comprising a polypeptide fusion construct of claim 1 and one or more pharmaceutically acceptable carriers or excipients.

21. The method of claim 20, wherein said subject in need thereof is a human.

22. The method of claim 20, wherein said effective amount of the polypeptide fusion construct ranges from 0.1 mg/Kg/day to 30 mg/Kg/day.

23. The method of claim 20, wherein said composition is administered in a form selected from the group consisting of oral, rectal, nasal, parenteral, intracisternal, intravaginal, intraperitoneal, sublingual, topical, and bucal administration.

24. The method of claim 20, wherein said composition is administered intravenously.

25. The polypeptide fusion construct of claim 1, wherein said amino acid sequence is identical to a sequence selected from the group consisting of SEQ ID NO: 3, SEQ ID NO: 7, SEQ ID NO: 14, SEQ ID NO:16, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, and SEQ ID NO: 39.

26. The polypeptide fusion construct of claim 1, wherein said amino acid sequence is a variant having one amino acid substitution in a sequence selected from the group consisting of SEQ ID NO: 3, SEQ ID NO: 7, SEQ ID NO:14, SEQ ID NO: 16, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, and SEQ ID NO: 39.

27. The polypeptide fusion construct of claim 1, wherein said amino acid sequence is SEQ ID NO: 14 or SEQ ID NO: 16.

28. The polypeptide fusion construct of claim 1, wherein said peptide having high transduction potential comprises a peptide other than ANT (SEQ ID NO: 1).

* * * * *

SEQUENCE LISTING

```
<160> NUMBER OF SEQ ID NOS: 39

<210> SEQ ID NO 1
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 1

Cys Arg Gln Ile Lys Ile Trp Phe Gln Asn Arg Arg Met Lys Trp Lys
1               5                   10                  15

Lys

<210> SEQ ID NO 2
<211> LENGTH: 57
<212> TYPE: PRT
<213> ORGANISM: Artificial Sequence
```

```
<220> FEATURE:
<223> OTHER INFORMATION: Synthetic Peptide

<400> SEQUENCE: 2

Cys Arg Gln Ile Lys Ile Trp Phe Gln Asn Arg Arg Met Lys Trp Lys
1               5                   10                  15

Lys Ser Lys Gly Met Gln Leu Gln Asp Leu Arg Gln Gln Leu Gln Gln
            20                  25                  30

Ala Glu Glu Ala Leu Val Ala Lys Gln Glu Leu Ile Asp Lys Leu Lys
        35                  40                  45

Glu Glu Ala Glu Gln His Lys Ile Val
    50                  55

<210> SEQ ID NO 3
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 3

Ser Lys Gly Met Gln Leu Glu Asp Leu Arg Gln Gln Leu Gln Gln Ala
1               5                   10                  15

Glu Glu Ala Leu Val Ala Lys Gln Glu Leu Ile Asp Lys Leu Lys Glu
            20                  25                  30

Glu Ala Glu Gln His Lys Ile Val
        35                  40

<210> SEQ ID NO 4
<211> LENGTH: 57
<212> TYPE: PRT
<213> ORGANISM: Artificial Sequence
<220> FEATURE:
<223> OTHER INFORMATION: Synthetic Peptide

<400> SEQUENCE: 4

Cys Arg Gln Ile Lys Ile Trp Phe Gln Asn Arg Arg Met Lys Trp Lys
1               5                   10                  15

Lys Ser Lys Gly Met Gln Leu Glu Asp Leu Arg Gln Gln Gly Gln Gln
            20                  25                  30

Ala Glu Glu Ala Gly Val Ala Lys Gln Glu Leu Gly Asp Lys Leu Lys
        35                  40                  45

Glu Glu Ala Glu Gln His Lys Ile Val
    50                  55

<210> SEQ ID NO 5
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 5

Ser Lys Gly Met Gln Leu Glu Asp Leu Arg Gln Gln Gly Gln Gln Ala
1               5                   10                  15

Glu Glu Ala Gly Val Ala Lys Gln Glu Leu Gly Asp Lys Leu Lys Glu
            20                  25                  30

Glu Ala Glu Gln His Lys Ile Val
        35                  40

<210> SEQ ID NO 6
```

```
<211> LENGTH: 60
<212> TYPE: PRT
<213> ORGANISM: Artificial Sequence
<220> FEATURE:
<223> OTHER INFORMATION: Synthetic Peptide

<400> SEQUENCE: 6

Cys Arg Gln Ile Lys Ile Trp Phe Gln Asn Arg Arg Met Lys Trp Lys
1               5                   10                  15

Lys Leu Lys Ala Gln Ala Asp Ile Tyr Lys Ala Asp Phe Gln Ala Glu
            20                  25                  30

Arg His Ala Arg Glu Lys Leu Val Glu Lys Glu Tyr Leu Gln Glu
        35                  40                  45

Gln Leu Glu Gln Leu Gln Arg Glu Phe Asn Lys Leu
    50                  55                  60

<210> SEQ ID NO 7
<211> LENGTH: 43
<212> TYPE: PRT
<213> ORGANISM: Artificial Sequence
<220> FEATURE:
<223> OTHER INFORMATION: Synthetic Peptide

<400> SEQUENCE: 7

Leu Lys Ala Gln Ala Asp Ile Tyr Lys Ala Asp Phe Gln Ala Glu Arg
1               5                   10                  15

His Ala Arg Glu Lys Leu Val Glu Lys Lys Glu Tyr Leu Gln Glu Gln
            20                  25                  30

Leu Glu Gln Leu Gln Arg Glu Phe Asn Lys Leu
        35                  40

<210> SEQ ID NO 8
<211> LENGTH: 60
<212> TYPE: PRT
<213> ORGANISM: Artificial Sequence
<220> FEATURE:
<223> OTHER INFORMATION: Synthetic Peptide

<400> SEQUENCE: 8

Cys Arg Gln Ile Lys Ile Trp Phe Gln Asn Arg Arg Met Lys Trp Lys
1               5                   10                  15

Lys Leu Lys Ala Gln Ala Asp Ile Tyr Lys Ala Asp Phe Gln Ala Glu
            20                  25                  30

Arg His Ala Arg Glu Lys Leu Val Glu Lys Lys Glu Tyr Ser Gln Glu
        35                  40                  45

Gln Leu Glu Gln Ser Gln Arg Glu Phe Asn Lys Leu
    50                  55                  60

<210> SEQ ID NO 9
<211> LENGTH: 43
<212> TYPE: PRT
<213> ORGANISM: Artificial Sequence
<220> FEATURE:
<223> OTHER INFORMATION: Synthetic Peptide

<400> SEQUENCE: 9

Leu Lys Ala Gln Ala Asp Ile Tyr Lys Ala Asp Phe Gln Ala Glu Arg
1               5                   10                  15

His Ala Arg Glu Lys Leu Val Glu Lys Lys Glu Tyr Ser Gln Glu Glu
            20                  25                  30

Leu Glu Gln Ser Gln Arg Glu Phe Asn Lys Leu
        35                  40
```

<210> SEQ ID NO 10
<211> LENGTH: 55
<212> TYPE: PRT
<213> ORGANISM: Artificial Sequence
<220> FEATURE:
<223> OTHER INFORMATION: Synthetic Peptide

<400> SEQUENCE: 10

```
Cys Arg Gln Ile Lys Ile Trp Phe Gln Asn Arg Arg Met Lys Trp Lys
1               5                   10                  15
Lys Ser Lys Gly Met Gln Arg Met Lys Gln Leu Glu Asp Lys Val Glu
            20                  25                  30
Glu Leu Leu Ser Lys Asn Tyr His Leu Glu Asn Glu Val Ala Arg Leu
        35                  40                  45
Lys Lys Leu Val Gly Glu Arg
    50                  55
```

<210> SEQ ID NO 11
<211> LENGTH: 1239
<212> TYPE: DNA
<213> ORGANISM: Mus musculus

<400> SEQUENCE: 11

| | |
|---|---|
| atgaacaagc accctggaa gaaccagctg agtgagacgg tgcagcccag tggtggccca | 60 |
| gcagaggacc aggacatgct gggtgaagaa tcttctctgg ggagcctgca atgctacatc | 120 |
| tgccttcaga gcagggtact cctgagaccc tccagcgctg cctggaagag aatcaagagc | 180 |
| tccgagacgc tatccggcag agcaatcaga tgctgaggga acgctgtgag gagctgctgc | 240 |
| atttccaggt cagccagcgg gaggagaagg agttccttat gtgcaaattc caggaagccc | 300 |
| ggaagctggt ggagagactg agcttggaga agcttgatct tcggagtcag agggaacagg | 360 |
| ccttaaagga gttggagcaa ctgaagaaat gccaacagca gatggctgag acaaggcct | 420 |
| ctgtgaaagc tcaggtgaca tcattgctcg agaactccag ggagagccag agccgtttgg | 480 |
| aggctgccac caaggatcgg caagctttag agggaaggat tcgagcagtt agtgagcagg | 540 |
| tcagacagct ggagagtgag cgggaggtgc tacagcagca gcacagcgtc caggtggacc | 600 |
| agctgcgtat gcagaaccag agcgtggagg ctgccttgcg aatggagcgg caggctgctt | 660 |
| cagaggagaa gcggaagctg gctcagttgc aggcagccta tcaccaactc ttccaagact | 720 |
| acgacagcca cattaagagc agcaagggca tgcagctgga agatctgagg ccaacagctc | 780 |
| cagcaagctg aggaggccct ggtagccaaa caggaattga ttgataagct gaaagaggag | 840 |
| gctgagcagc acaagattgt gatggagact gtgccagtct tgaaggccca ggcggatatc | 900 |
| tacaaggctg acttccaaag ctgagaggca tgcccgggag aagctggtgg agaagaagga | 960 |
| gtatttgcag gagcagctgg agcagctgca gcgcgagttc aacaagctga agttggctg | 1020 |
| ccatgagtca gccaggattg aggatatgag gaagcggcat gtagagactc cccagcctcc | 1080 |
| tttactccct gctccagctc accactcctt tcatttggcc ttgtccaacc agcggaggag | 1140 |
| ccctcctgaa gaacctcctg acttctgttg tccgaagtgc agtatcggc tcctgatatg | 1200 |
| gacactctac agatacatgt catggagtgc atagagtag | 1239 |

<210> SEQ ID NO 12
<211> LENGTH: 412
<212> TYPE: PRT
<213> ORGANISM: Mus musculus

```
<400> SEQUENCE: 12

Met Asn Lys His Pro Trp Lys Asn Gln Leu Ser Glu Thr Val Gln Pro
1               5                   10                  15

Ser Gly Gly Pro Ala Glu Asp Gln Asp Met Leu Gly Glu Glu Ser Ser
            20                  25                  30

Leu Gly Lys Pro Ala Met Leu His Leu Pro Ser Glu Gln Gly Thr Pro
        35                  40                  45

Glu Thr Leu Gln Arg Cys Leu Glu Asn Gln Glu Leu Arg Asp Ala
    50                  55                  60

Ile Arg Gln Ser Asn Gln Met Leu Arg Glu Arg Cys Glu Glu Leu Leu
65                  70                  75                  80

His Phe Gln Val Ser Gln Arg Glu Glu Lys Glu Phe Leu Met Cys Lys
                85                  90                  95

Phe Gln Glu Ala Arg Lys Leu Val Glu Arg Leu Ser Leu Glu Lys Leu
            100                 105                 110

Asp Leu Arg Ser Gln Arg Glu Gln Ala Leu Lys Glu Leu Glu Leu
        115                 120                 125

Lys Lys Cys Gln Gln Gln Met Ala Glu Asp Lys Ala Ser Val Lys Ala
130                 135                 140

Gln Val Thr Ser Leu Leu Gly Glu Leu Gln Glu Ser Gln Ser Arg Leu
145                 150                 155                 160

Glu Ala Ala Thr Lys Asp Arg Gln Ala Leu Glu Gly Arg Ile Arg Ala
                165                 170                 175

Val Ser Glu Gln Val Arg Gln Leu Glu Ser Glu Arg Glu Val Leu Gln
            180                 185                 190

Gln Gln His Ser Val Gln Val Asp Gln Leu Arg Met Gln Asn Gln Ser
        195                 200                 205

Val Glu Ala Ala Leu Arg Met Glu Arg Gln Ala Ala Ser Glu Glu Lys
210                 215                 220

Arg Lys Leu Ala Gln Leu Gln Ala Ala Tyr His Gln Leu Phe Gln Asp
225                 230                 235                 240

Tyr Asp Ser His Ile Lys Ser Ser Lys Gly Met Gln Leu Glu Asp Leu
                245                 250                 255

Arg Gln Gln Leu Gln Gln Ala Glu Glu Ala Leu Val Ala Lys Gln Glu
            260                 265                 270

Leu Ile Asp Lys Leu Lys Glu Glu Ala Glu Gln His Lys Ile Val Met
        275                 280                 285

Glu Thr Val Pro Val Leu Lys Ala Gln Ala Asp Ile Tyr Lys Ala Asp
290                 295                 300

Phe Gln Ala Glu Arg His Ala Arg Glu Lys Leu Val Glu Lys Lys Glu
305                 310                 315                 320

Tyr Leu Gln Glu Gln Leu Glu Gln Leu Gln Arg Glu Phe Asn Lys Leu
                325                 330                 335

Lys Val Gly Cys His Glu Ser Ala Arg Ile Glu Asp Met Arg Lys Arg
            340                 345                 350

His Val Glu Thr Pro Gln Pro Leu Leu Pro Ala Pro Ala His His
        355                 360                 365

Ser Phe His Leu Ala Leu Ser Asn Gln Arg Arg Ser Pro Pro Glu Glu
        370                 375                 380

Pro Pro Asp Phe Cys Cys Pro Lys Cys Gln Tyr Gln Ala Pro Asp Met
385                 390                 395                 400

Asp Thr Leu Gln Ile His Val Met Glu Cys Ile Glu
                405                 410
```

<210> SEQ ID NO 13
<211> LENGTH: 57
<212> TYPE: PRT
<213> ORGANISM: Artificial Sequence
<220> FEATURE:
<223> OTHER INFORMATION: Synthetic Peptide

<400> SEQUENCE: 13

Cys Arg Gln Ile Lys Ile Trp Phe Gln Asn Arg Arg Met Lys Trp Lys
1               5                   10                  15

Lys Ser Lys Gly Met Gln Leu Glu Asp Leu Lys Gln Gln Leu Gln Gln
            20                  25                  30

Ala Glu Glu Ala Leu Val Ala Lys Gln Glu Val Ile Asp Lys Leu Lys
        35                  40                  45

Glu Glu Ala Glu Gln His Lys Ile Val
    50                  55

<210> SEQ ID NO 14
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 14

Ser Lys Gly Met Gln Leu Glu Asp Leu Lys Gln Gln Leu Gln Gln Ala
1               5                   10                  15

Glu Glu Ala Leu Val Ala Lys Gln Glu Val Ile Asp Lys Leu Lys Glu
            20                  25                  30

Glu Ala Glu Gln His Lys Ile Val
        35                  40

<210> SEQ ID NO 15
<211> LENGTH: 60
<212> TYPE: PRT
<213> ORGANISM: Artificial Sequence
<220> FEATURE:
<223> OTHER INFORMATION: Synthetic Peptide

<400> SEQUENCE: 15

Cys Arg Gln Ile Lys Ile Trp Phe Gln Asn Arg Arg Met Lys Trp Lys
1               5                   10                  15

Lys Leu Lys Ala Gln Ala Asp Ile Tyr Lys Ala Asp Phe Gln Ala Glu
            20                  25                  30

Arg Gln Ala Arg Glu Lys Leu Ala Glu Lys Lys Glu Leu Leu Gln Glu
        35                  40                  45

Gln Leu Glu Gln Leu Gln Arg Glu Tyr Ser Lys Leu
    50                  55                  60

<210> SEQ ID NO 16
<211> LENGTH: 43
<212> TYPE: PRT
<213> ORGANISM: Artificial Sequence
<220> FEATURE:
<223> OTHER INFORMATION: Synthetic Peptide

<400> SEQUENCE: 16

Leu Lys Ala Gln Ala Asp Ile Tyr Lys Ala Asp Phe Gln Ala Glu Arg
1               5                   10                  15

Gln Ala Arg Glu Lys Leu Ala Glu Lys Lys Glu Leu Leu Gln Glu Gln
            20                  25                  30

Leu Glu Gln Leu Gln Arg Glu Tyr Ser Lys Leu
        35                  40

<210> SEQ ID NO 17
<211> LENGTH: 2035
<212> TYPE: DNA
<213> ORGANISM: Homo sapiens

<400> SEQUENCE: 17

| | | | | | |
|---|---|---|---|---|---|
| cgagctggac | tgtttctact | cctccctcct | cctccactgc | ggggtctgac | cctactcctt | 60 |
| gtgtgaggac | tcctctagtt | cagagacata | ttctgttcac | caaacttgac | tgcgctctat | 120 |
| cgaggtcgtt | aaattcttcg | gaaatgcctc | acatatagtt | tggcagctag | cccttgccct | 180 |
| gttggatgaa | taggcacctc | tggaagagcc | aactgtgtga | gatggtgcag | cccagtggtg | 240 |
| gcccggcagc | agatcaggac | gtactgggcg | aagagtctcc | tctggggaag | ccagccatgc | 300 |
| tgcacctgcc | ttcagaacag | ggcgctcctg | agaccctcca | gcgctgcctg | gaggagaatc | 360 |
| aagagctccg | agatgccatc | cggcagagca | accagattct | gcgggagcgc | tgcgaggagc | 420 |
| ttctgcattt | ccaagccagc | cagagggagg | agaaggagtt | cctcatgtgc | aagttccagg | 480 |
| aggccaggaa | actggtggag | agactcggcc | tggagaagct | cgatctgaag | aggcagaagg | 540 |
| agcaggctct | gcgggaggtg | gagcacctga | agagatgcca | gcagcagatg | gctgaggaca | 600 |
| aggcctctgt | gaaagcccag | gtgacgtcct | gctcgggga | gctgcaggag | agccagagtc | 660 |
| gcttggaggc | tgccactaag | gaatgccagg | ctctggaggg | tcgggcccgg | cggccagcg | 720 |
| agcaggcgcg | gcagctggag | agtgagcgcg | aggcgctgca | gcagcagcac | agcgtgcagg | 780 |
| tggaccagct | gcgcatgcag | ggccagagcg | tggaggccgc | gctccgcatg | gagcgccagg | 840 |
| ccgcctcgga | ggagaagagg | aagctggccc | agttgcaggt | ggcctatcac | cagctcttcc | 900 |
| aagaatacga | caaccacatc | aagagcagcg | tggtgggcag | tgagcggaag | cgaggaatgc | 960 |
| agctggaaga | tctcaaacag | cagctccagc | aggccgagga | ggccctggtg | ccaaacagg | 1020 |
| aggtgatcga | taagctgaag | gaggaggccg | agcagcacaa | gattgtgatg | agaccgttc | 1080 |
| cggtgctgaa | ggcccaggcg | gatatctaca | aggcggactt | ccaggctgag | aggcaggccc | 1140 |
| gggagaagct | ggccgagaag | aaggagctcc | tgcaggagca | gctggagcag | ctgcagaggg | 1200 |
| agtacagcaa | actgaaggcc | agctgtcagg | agtcggccag | gatcgaggac | atgaggaagc | 1260 |
| ggcatgtcga | ggtctcccag | gccccccttgc | ccccgcccc | tgcctacctc | tcctctcccc | 1320 |
| tggccctgcc | cagccagagg | aggagcccc | ccgaggagcc | acctgacttc | tgctgtccca | 1380 |
| agtgccagta | tcaggcccct | gatatggaca | cctgcagat | acatgtcatg | gagtgcattg | 1440 |
| agtagggccg | gccagtgcaa | ggccactgcc | tgccgaggac | gtgcccggga | ccgtgcagtc | 1500 |
| tgcgctttcc | tctcccgcct | gcctagccca | ggatgaaggg | ctgggtggcc | acaactggga | 1560 |
| tgccacctgg | agcccaccc | aggagctggc | cgcggcacct | tacgcttcag | ctgttgatcc | 1620 |
| gctggtcccc | tcttttgggg | tagatgcggc | cccgatcagg | cctgactcgc | tgctctttt | 1680 |
| gttcccttct | gtctgctcga | accacttgcc | tcgggctaat | ccctccctct | tcctccaccc | 1740 |
| ggcactgggg | aagtcaagaa | tggggcctgg | ggctctcagg | gagaactgct | tccctggca | 1800 |
| gagctgggtg | gcagctcttc | ctcccaccgg | acaccgaccc | gcccgctgct | gtgccctggg | 1860 |
| agtgctgccc | tcttaccatg | cacacggtg | ctctccttt | gggctgcatg | ctattccatt | 1920 |
| ttgcagccag | accgatgtgt | atttaaccag | tcactattga | tggacatttg | ggttgtttcc | 1980 |
| catcttttg | ttaccataaa | taatggcata | gtaaaaatcc | ttgtgcatta | aaaaa | 2035 |

<210> SEQ ID NO 18
<211> LENGTH: 419
<212> TYPE: PRT
<213> ORGANISM: Homo sapiens

<400> SEQUENCE: 18

```
Met Asn Arg His Leu Trp Lys Ser Gln Leu Cys Glu Met Val Gln Pro
1               5                   10                  15

Ser Gly Gly Pro Ala Ala Asp Gln Asp Val Leu Gln Glu Glu Ser Pro
            20                  25                  30

Leu Gly Lys Pro Ala Met Leu His Leu Pro Ser Glu Gln Gly Ala Pro
        35                  40                  45

Glu Thr Leu Gln Arg Cys Leu Glu Glu Asn Gln Glu Leu Arg Asp Ala
    50                  55                  60

Ile Arg Gln Ser Asn Gln Ile Leu Arg Glu Arg Cys Glu Glu Leu Leu
65                  70                  75                  80

His Phe Gln Ala Ser Gln Arg Glu Glu Lys Glu Phe Leu Met Cys Lys
                85                  90                  95

Phe Gln Glu Ala Arg Lys Leu Val Glu Arg Leu Gly Leu Glu Lys Leu
            100                 105                 110

Asp Leu Lys Arg Gln Lys Glu Gln Ala Leu Arg Glu Val Glu His Leu
        115                 120                 125

Lys Arg Cys Gln Gln Gln Met Ala Glu Asp Lys Ala Ser Val Lys Ala
130                 135                 140

Gln Val Thr Ser Leu Leu Gly Glu Leu Gln Glu Ser Gln Ser Arg Leu
145                 150                 155                 160

Glu Ala Ala Thr Lys Glu Cys Gln Ala Leu Glu Gly Arg Ala Arg Ala
                165                 170                 175

Ala Ser Glu Gln Ala Arg Gln Leu Glu Ser Glu Arg Glu Ala Leu Gln
            180                 185                 190

Gln Gln His Ser Val Gln Val Asp Gln Leu Arg Met Gln Gly Gln Ser
        195                 200                 205

Val Glu Ala Ala Leu Arg Met Glu Arg Gln Ala Ala Ser Glu Glu Lys
    210                 215                 220

Arg Lys Leu Ala Gln Leu Gln Val Ala Tyr His Gln Leu Phe Gln Glu
225                 230                 235                 240

Trp Asp Asn His Ile Lys Ser Ser Val Val Gly Ser Glu Arg Lys Arg
                245                 250                 255

Gly Met Gln Leu Glu Asp Leu Lys Gln Gln Leu Gln Gln Ala Glu Glu
            260                 265                 270

Ala Leu Val Ala Lys Gln Glu Val Ile Asp Lys Leu Lys Glu Glu Ala
        275                 280                 285

Glu Gln His Lys Ile Val Met Glu Thr Val Pro Val Leu Lys Ala Gln
    290                 295                 300

Ala Asp Ile Tyr Lys Ala Asp Phe Gln Ala Glu Arg Gln Ala Arg Glu
305                 310                 315                 320

Lys Leu Ala Glu Lys Lys Glu Leu Leu Gln Gln Leu Glu Gln Leu
                325                 330                 335

Gln Arg Glu Tyr Ser Lys Leu Lys Ala Ser Cys Gln Glu Ser Ala Arg
            340                 345                 350

Ile Glu Asp Met Arg Lys Arg His Val Glu Val Ser Gln Ala Pro Leu
        355                 360                 365

Pro Pro Ala Pro Ala Tyr Leu Ser Ser Pro Leu Ala Leu Pro Ser Gln
```

```
                    370                 375                 380
Arg Arg Ser Pro Pro Glu Glu Pro Pro Asp Phe Cys Cys Pro Lys Cys
385                 390                 395                 400

Gln Tyr Gln Ala Pro Asp Met Asp Thr Leu Gln Ile His Val Met Glu
            405                 410                 415

Cys Ile Glu

<210> SEQ ID NO 19
<211> LENGTH: 51
<212> TYPE: PRT
<213> ORGANISM: Mus musculus

<400> SEQUENCE: 19

Glu Leu Ile Asp Lys Leu Lys Glu Glu Ala Glu Gln His Lys Ile Val
1               5                   10                  15

Met Glu Thr Val Pro Val Leu Lys Ala Gln Ala Asp Ile Tyr Lys Ala
            20                  25                  30

Asp Phe Gln Ala Glu Arg His Ala Arg Glu Lys Leu Val Glu Lys Lys
        35                  40                  45

Glu Tyr Leu
    50

<210> SEQ ID NO 20
<211> LENGTH: 51
<212> TYPE: PRT
<213> ORGANISM: Homo sapiens

<400> SEQUENCE: 20

Glu Val Ile Asp Lys Leu Lys Glu Glu Ala Glu Gln His Lys Ile Val
1               5                   10                  15

Met Glu Thr Val Pro Val Leu Lys Ala Gln Ala Asp Ile Tyr Lys Ala
            20                  25                  30

Asp Phe Gln Ala Glu Arg Gln Ala Arg Glu Lys Leu Ala Glu Lys Lys
        35                  40                  45

Glu Leu Leu
    50

<210> SEQ ID NO 21
<211> LENGTH: 51
<212> TYPE: PRT
<213> ORGANISM: Bos taurus

<400> SEQUENCE: 21

Glu Val Ile Asp Lys Leu Lys Glu Glu Ala Glu Gln His Lys Ile Val
1               5                   10                  15

Met Glu Thr Val Pro Val Leu Lys Ala Gln Ala Asp Ile Tyr Lys Ala
            20                  25                  30

Asp Phe Gln Ala Glu Arg Gln Ala Arg Glu Lys Leu Ala Glu Lys Lys
        35                  40                  45

Glu Phe Leu
    50

<210> SEQ ID NO 22
<211> LENGTH: 55
<212> TYPE: PRT
<213> ORGANISM: Drosphilia melanogaster

<400> SEQUENCE: 22

Glu Leu Ile Lys Lys Met Gln Leu Asp Ile Asn Glu Leu Lys Ala Arg
```

```
                1               5                  10                 15
Asp Ile Gln Lys Gln Glu Val Ile Lys Gly Leu Gln Ile Gln Asn Asp
            20                  25                 30

Ile Tyr Arg Arg Asp Phe Glu Met Glu Arg Ala Asp Arg Glu Lys Asn
            35                  40                 45

Ala Gly Glu Lys Asp Gln Tyr
            50              55

<210> SEQ ID NO 23
<211> LENGTH: 51
<212> TYPE: PRT
<213> ORGANISM: Mus musculus

<400> SEQUENCE: 23

Leu Gln Met Asp Glu Met Lys Gln Thr Leu Ala Lys Gln Glu Glu Asp
1               5                   10                 15

Leu Glu Thr Met Ala Val Leu Arg Ala Gln Met Glu Val Tyr Cys Ser
            20                  25                 30

Asp Phe His Ala Glu Arg Ala Ala Arg Glu Lys Ile His Glu Glu Lys
            35                  40                 45

Glu Gln Leu
    50

<210> SEQ ID NO 24
<211> LENGTH: 51
<212> TYPE: PRT
<213> ORGANISM: Homo sapiens

<400> SEQUENCE: 24

Leu Gln Met Asp Glu Met Lys Gln Thr Ile Ala Lys Gln Glu Glu Asp
1               5                   10                 15

Leu Glu Thr Met Thr Ile Leu Arg Ala Gln Met Glu Val Tyr Cys Ser
            20                  25                 30

Asp Phe His Ala Glu Arg Ala Ala Arg Glu Lys Ile His Glu Glu Lys
            35                  40                 45

Glu Gln Leu
    50

<210> SEQ ID NO 25
<211> LENGTH: 59
<212> TYPE: PRT
<213> ORGANISM: Mus musculus

<400> SEQUENCE: 25

Ser Pro Ser Ser Pro Pro Ala Ala Phe Gly Ser Pro Glu Gly Val Gly
1               5                   10                 15

Gly His Leu Arg Lys Gln Glu Leu Val Thr Gln Asn Glu Leu Leu Lys
            20                  25                 30

Gln Gln Val Lys Ile Phe Glu Glu Asp Phe Gln Arg Glu Arg Ser Asp
            35                  40                 45

Arg Glu Arg Met Asn Glu Glu Lys Glu Glu Leu
    50                  55

<210> SEQ ID NO 26
<211> LENGTH: 59
<212> TYPE: PRT
<213> ORGANISM: Homo sapiens

<400> SEQUENCE: 26
```

```
Pro Pro Ser Ser Pro Pro Thr Ala Phe Gly Ser Pro Glu Gly Ala Gly
1               5                   10                  15

Ala Leu Leu Arg Lys Gln Glu Leu Val Thr Gln Asn Glu Leu Leu Lys
            20                  25                  30

Gln Gln Val Lys Ile Phe Glu Glu Asp Phe Gln Arg Glu Arg Ser Asp
            35                  40                  45

Arg Glu Arg Met Asn Glu Glu Lys Glu Glu Leu
    50                  55
```

<210> SEQ ID NO 27
<211> LENGTH: 51
<212> TYPE: PRT
<213> ORGANISM: Mus musculus

<400> SEQUENCE: 27

```
Glu Ala Asn Gln Glu Leu Thr Ala Met Arg Met Ser Arg Asp Thr Ala
1               5                   10                  15

Leu Glu Arg Val Gln Met Leu Glu Gln Gln Ile Leu Ala Tyr Lys Asp
            20                  25                  30

Asp Phe Lys Ser Glu Arg Ala Asp Arg Glu Arg Ala His Ser Arg Ile
            35                  40                  45

Gln Glu Leu
    50
```

<210> SEQ ID NO 28
<211> LENGTH: 51
<212> TYPE: PRT
<213> ORGANISM: Homo sapiens

<400> SEQUENCE: 28

```
Glu Val Lys Gln Glu Leu Ala Ala Ser Arg Thr Ala Arg Asp Ala Ala
1               5                   10                  15

Leu Glu Arg Val Gln Met Leu Glu Gln Gln Ile Leu Ala Tyr Lys Asp
            20                  25                  30

Asp Phe Met Ser Glu Arg Ala Asp Arg Glu Arg Ala Gln Ser Arg Ile
            35                  40                  45

Gln Glu Leu
    50
```

<210> SEQ ID NO 29
<211> LENGTH: 54
<212> TYPE: PRT
<213> ORGANISM: Homo sapiens

<400> SEQUENCE: 29

```
Ser Phe Ser Glu Asp Cys Leu Arg Lys Ser Arg Val Glu Phe Cys His
1               5                   10                  15

Glu Glu Met Arg Thr Glu Met Glu Val Leu Lys Gln Gln Val Gln Ile
            20                  25                  30

Tyr Glu Glu Asp Phe Lys Lys Glu Arg Ser Asp Arg Glu Arg Leu Asn
            35                  40                  45

Gln Glu Lys Glu Glu Leu
    50
```

<210> SEQ ID NO 30
<211> LENGTH: 21
<212> TYPE: PRT
<213> ORGANISM: Artificial Sequence
<220> FEATURE:
<223> OTHER INFORMATION: Synthetic Peptide

```
<400> SEQUENCE: 30

Leu Lys Ala Gln Ala Asp Ile Tyr Lys Ala Arg Phe Gln Ala Glu Arg
1               5                   10                  15

His Ala Arg Glu Lys
            20

<210> SEQ ID NO 31
<211> LENGTH: 38
<212> TYPE: PRT
<213> ORGANISM: Artificial Sequence
<220> FEATURE:
<223> OTHER INFORMATION: Synthetic Peptide

<400> SEQUENCE: 31

Cys Arg Gln Ile Lys Ile Trp Phe Gln Asn Arg Arg Met Lys Trp Lys
1               5                   10                  15

Lys Leu Lys Ala Gln Ala Asp Ile Tyr Lys Ala Arg Phe Gln Ala Glu
            20                  25                  30

Arg His Ala Arg Glu Lys
        35

<210> SEQ ID NO 32
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 32

Cys Tyr Gly Arg Lys Lys Arg Arg Gln Arg Arg Arg Leu Lys Ala Gln
1               5                   10                  15

Ala Asp Ile Tyr Lys Ala Arg Phe Gln Ala Glu Arg His Ala Arg Glu
            20                  25                  30

Lys

<210> SEQ ID NO 33
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 33

Cys Arg Arg Arg Arg Arg Arg Arg Leu Lys Ala Gln Ala Asp Ile Tyr
1               5                   10                  15

Lys Ala Arg Phe Gln Ala Glu Arg His Ala Arg Glu Lys
            20                  25

<210> SEQ ID NO 34
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 34

Cys Arg Arg Arg Arg Arg Arg Arg Arg Arg Leu Lys Ala Gln Ala Asp
1               5                   10                  15

Ile Tyr Lys Ala Arg Phe Gln Ala Glu Arg His Ala Arg Glu Lys
            20                  25                  30
```

-continued

```
<210> SEQ ID NO 35
<211> LENGTH: 21
<212> TYPE: PRT
<213> ORGANISM: Homo sapiens

<400> SEQUENCE: 35

Leu Lys Ala Gln Ala Asp Ile Tyr Lys Ala Arg Phe Gln Ala Glu Arg
1               5                   10                  15

Gln Ala Arg Glu Lys
            20

<210> SEQ ID NO 36
<211> LENGTH: 38
<212> TYPE: PRT
<213> ORGANISM: Homo sapiens

<400> SEQUENCE: 36

Cys Arg Gln Ile Lys Ile Trp Phe Gln Asn Arg Arg Met Lys Trp Lys
1               5                   10                  15

Lys Leu Lys Ala Gln Ala Asp Ile Tyr Lys Ala Arg Phe Gln Ala Glu
            20                  25                  30

Arg Gln Ala Arg Glu Lys
            35

<210> SEQ ID NO 37
<211> LENGTH: 33
<212> TYPE: PRT
<213> ORGANISM: Homo sapiens

<400> SEQUENCE: 37

Cys Tyr Gly Arg Lys Lys Arg Arg Gln Arg Arg Arg Leu Lys Ala Gln
1               5                   10                  15

Ala Asp Ile Tyr Lys Ala Arg Phe Gln Ala Glu Arg Gln Ala Arg Glu
            20                  25                  30

Lys

<210> SEQ ID NO 38
<211> LENGTH: 29
<212> TYPE: PRT
<213> ORGANISM: Homo sapiens

<400> SEQUENCE: 38

Cys Arg Arg Arg Arg Arg Arg Arg Leu Lys Ala Gln Ala Asp Ile Tyr
1               5                   10                  15

Lys Ala Arg Phe Gln Ala Glu Arg Gln Ala Arg Glu Lys
            20                  25

<210> SEQ ID NO 39
<211> LENGTH: 31
<212> TYPE: PRT
<213> ORGANISM: Homo sapiens

<400> SEQUENCE: 39

Cys Arg Arg Arg Arg Arg Arg Arg Arg Arg Leu Lys Ala Gln Ala Asp
1               5                   10                  15

Ile Tyr Lys Ala Arg Phe Gln Ala Glu Arg Gln Ala Arg Glu Lys
            20                  25                  30
```